US010099057B2

United States Patent
Kent et al.

(10) Patent No.: US 10,099,057 B2
(45) Date of Patent: Oct. 16, 2018

(54) SYSTEM AND METHOD FOR DETERMINING NEURONAL SYSTEM RESPONSE

(71) Applicant: PACESETTER, INC., Sylmar, CA (US)

(72) Inventors: Alexander Kent, Mountain View, CA (US); Gene A. Bornzin, Simi Valley, CA (US); Edward Karst, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 14 days.

(21) Appl. No.: 15/356,360

(22) Filed: Nov. 18, 2016

(65) Prior Publication Data

US 2018/0140843 A1 May 24, 2018

(51) Int. Cl.
*A61N 1/36* (2006.01)
*A61N 1/372* (2006.01)
*A61N 1/02* (2006.01)

(52) U.S. Cl.
CPC ......... *A61N 1/36139* (2013.01); *A61N 1/025* (2013.01); *A61N 1/36071* (2013.01); *A61N 1/37264* (2013.01)

(58) Field of Classification Search
CPC ............... A61N 1/36139; A61N 1/025; A61N 1/36071; A61N 1/37264
See application file for complete search history.

(56) References Cited

U.S. PATENT DOCUMENTS

| | | | |
|---|---|---|---|
| 8,275,463 B1* | 9/2012 | Andersen | A61N 1/08 607/30 |
| 9,386,934 B2* | 7/2016 | Parker | A61N 1/36125 |
| 9,533,148 B2* | 1/2017 | Carcieri | A61N 1/36071 |
| 2011/0257708 A1* | 10/2011 | Kramer | A61N 1/0551 607/62 |
| 2013/0057436 A1* | 3/2013 | Krasner | G01S 19/11 342/464 |
| 2014/0236257 A1* | 8/2014 | Parker | A61B 5/04001 607/46 |
| 2017/0290515 A1* | 10/2017 | Butte | A61B 5/0071 |

* cited by examiner

Primary Examiner — Catherine Voorhees

(57) ABSTRACT

Systems and methods are provided for determining a system response for a neuronal region of interest (ROI). The method comprises positioning an electrode proximate to the neuronal ROI. The electrode is electrically coupled to a neurostimulation (NS) system. The system delivers, from the NS system, a stimulation waveform from the electrode based on NS parameters. The system further programs one or more processors for: measuring an evoked potential waveform resulting from the stimulation waveform; comparing at least one excitation pulse within the stimulation waveform to the evoked potential waveform to obtain a candidate response function; repeating the delivering, measuring and comparing operations to obtain a collection of candidate response functions; and identifying a neuronal system response for the neuronal ROI based on the collection of candidate response functions.

12 Claims, 15 Drawing Sheets

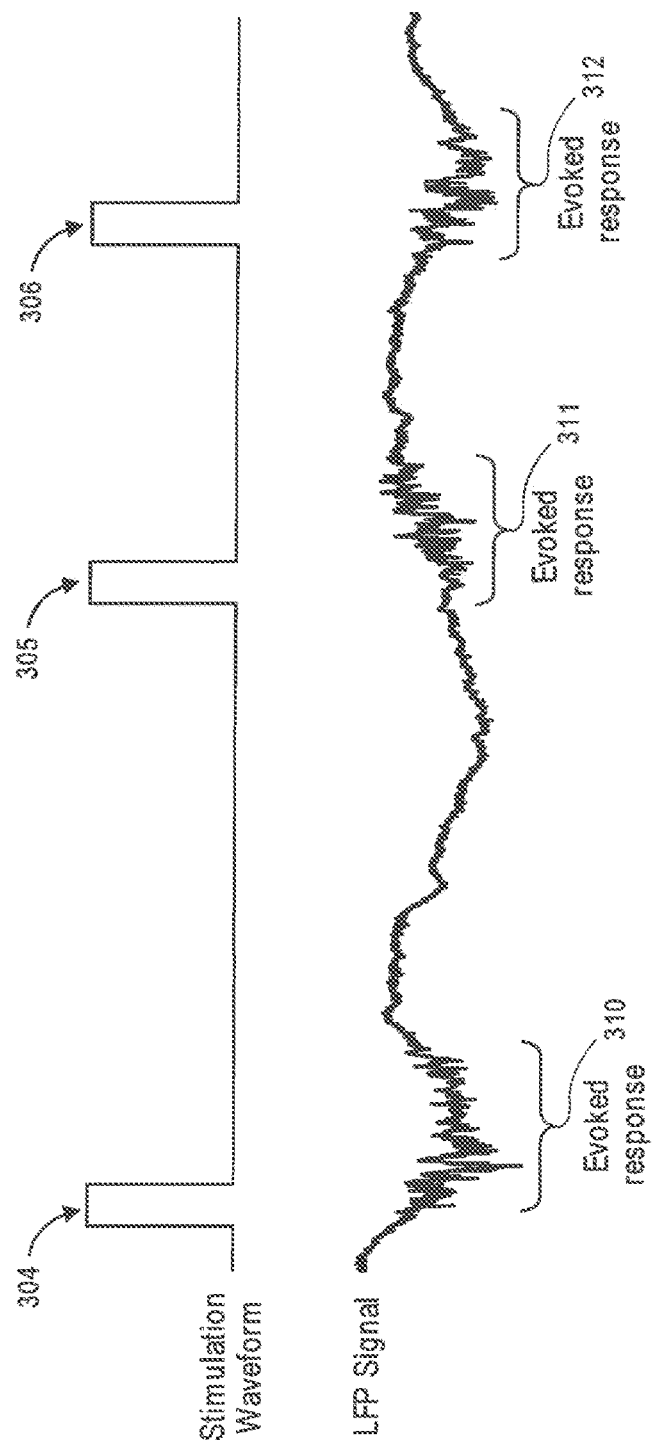

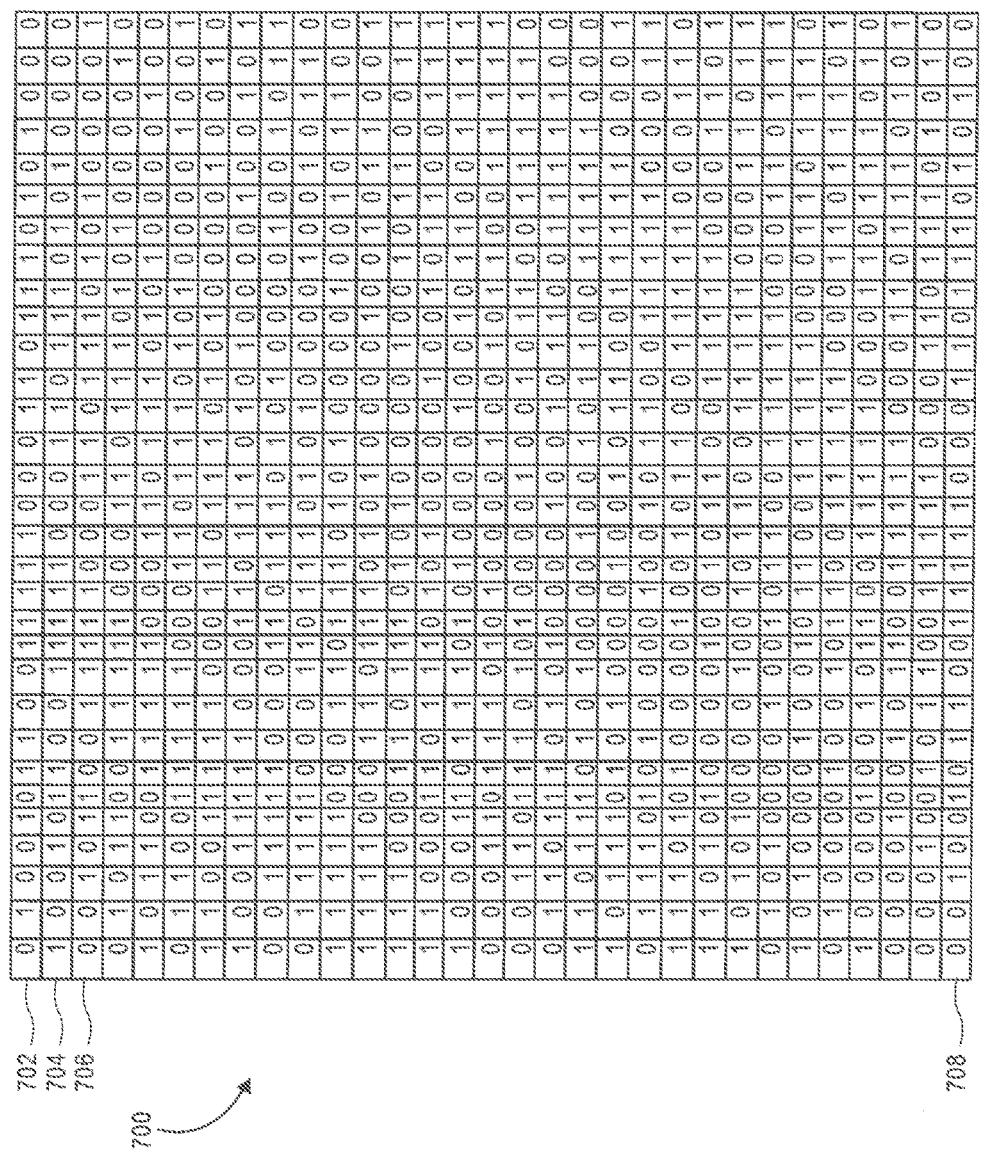

SYSTEM AND METHOD FOR DETERMINING NEURONAL SYSTEM RESPONSE

BACKGROUND OF THE INVENTION

Embodiments of the present disclosure generally relate to neurostimulation (NS) systems, and more particularly to systems and methods for analyzing evoked waveforms to determine a neuronal system response.

NS systems include devices that generate electrical pulses and deliver the pulses to nerve tissue to treat a variety of disorders via one or more electrodes. For example, spinal cord stimulation has been used to treat chronic and intractable pain. Another example is deep brain stimulation, which has been used to treat movement disorders such as Parkinson's disease and affective disorders such as depression. While a precise understanding of the interaction between the applied electrical energy and the nervous tissue is not fully appreciated, it is known that application of electrical pulses depolarize neurons and generate propagating action potentials into certain regions or areas of nerve tissue. The propagating action potentials effectively mask certain types of physiological neural activity, increase the production of neurotransmitters, or the like.

During stimulation by the NS systems, evoked potentials are emitted from the stimulated nerve tissue. The evoked potential signals may be generated by neuronal transmembrane currents of neurons activated following or in response to the NS. The simultaneous activation of multiple neurons generates a signal of sufficient amplitude for recording. The evoked potential signals propagate within the population of sensory nerve fibers through subsequent orthodromic or antidromic propagation from the excitation site.

It has been proposed that the neural signals recorded during electrical stimulation may provide feedback for adjustment of stimulation parameters in neuromodulation devices. For example, local field potentials (LFPs) are signals that are present within the brain and can be recorded from a deep brain stimulation (DBS) lead. It has been proposed that symptoms of movement disorders may be correlated to the LFP signal magnitude at specific signal frequencies, such as a beta band (13-35 Hz) in Parkinson's disease. Additionally, evoked potentials can be measured from spinal cord stimulation (SCS) leads. The amplitude of the evoked potential is related to the number of neurons in the spinal cord activated by SCS, and thereby indicates changes in the response to stimulation caused by movement of the SCS lead or other reasons.

However, recording neural activity can be challenging due to biological and external noise sources that obscure or confound recording of the signal of interest. Consequently, changes in the signal of interest may not be readily discernible, due to subtle shifts in amplitude, phase, or frequency. Moreover, the changes in the signal may be complex. For example, a change in signal amplitude at one frequency may correspond to a change in phase at a second frequency ("phase-amplitude coupling").

A need exists to overcome the shortcomings of conventional approaches to identify the neuronal system response to stimulation.

SUMMARY

In accordance with embodiments herein, a method is provided for determining a system response for a neuronal region of interest (ROI). The method comprises positioning an electrode proximate to the neuronal ROI. The electrode is electrically coupled to a neurostimulation (NS) system. The system delivers, from the NS system, a stimulation waveform from the electrode based on NS parameters. The system further programs one or more processors for: measuring an evoked potential waveform resulting from the stimulation waveform; comparing at least one excitation pulse within the stimulation waveform to the evoked potential waveform to obtain a candidate response function; repeating the delivering, measuring and comparing operations to obtain a collection of candidate response functions; and identifying a neuronal system response for the neuronal ROI based on the collection of candidate response functions.

Optionally, the candidate response functions may represent measures of a similarity of the excitation pulses and evoked potential waveforms as a function of a lag of the evoked potential waveforms relative to the corresponding excitation pulses. The method may further adjust the NS parameters based on the neuronal system response. The adjusting operation may comprise adjusting at least one of a stimulation frequency, amplitude, pulse width, contact configuration, and/or duty cycle based on the neuronal system response. The method may periodically adjust the NS parameters to define a patient specific stimulation waveform.

Optionally, the comparing operation may comprise performing a cross correlation analysis between the excitation pulses and the corresponding evoked potential waveforms to obtain the candidate response functions. The identifying operation may comprise identifying the neuronal system response in connection with at least one of deep brain stimulation, spinal cord stimulation, cortical stimulation, or peripheral nerve stimulation. The delivering operation may comprise delivering a series of excitation pulses within the stimulation waveform. The comparing operation may include applying a deconvolution matrix to the evoked potential waveforms in order to derive the candidate response functions. The stimulation waveform may include a series of pulses defined based on a pseudorandom binary sequence. The comparing operation may apply the pseudorandom binary sequence to the evoked potential waveforms in order to derive the candidate response functions.

In accordance with embodiments herein, a system is provided for determining a system response for a neuronal region of interest (ROI). The method comprises an electrode that is configured to be positioned proximate to the neuronal ROI. An implantable pulse generator (IPG) is electrically coupled to the electrode. The IPG is configured to deliver a stimulation waveform from the electrode based on NS parameters. The sensing circuitry is configured to measure an evoked potential waveform resulting from the stimulation waveform. One or more processors are configured to execute program instructions stored in memory, to: compare at least one excitation pulse within the stimulation waveform to the evoked potential waveform to obtain a candidate response function; repeat the delivering, measuring and comparing operations to obtain a collection of candidate response functions; and identify a neuronal system response for the neuronal ROI based on the collection of candidate response functions.

Optionally, the candidate response functions may represent measures of a similarity of the excitation pulses and evoked potential waveforms as a function of a lag of the evoked potential waveforms relative to the corresponding excitation pulses. The one or more processors may be configured to adjust the NS parameters based on the neuronal system response. The one or more processors may be configured to adjust at least one of a stimulation frequency, amplitude, pulse width, contact configuration, and/or duty cycle based on the neuronal system response. The one or more processors are configured to periodically adjust the NS parameters to define a patient specific stimulation waveform.

Optionally, the compare operation may comprise performing a cross correlation analysis between the excitation pulses and the corresponding evoked potential waveforms to obtain the candidate response functions. The identify operation may comprise identifying the neuronal system response in connection with at least one of deep brain stimulation, spinal cord stimulation, cortical stimulation, or peripheral nerve stimulation. The one or more processors may be configured to deliver a series of excitation pulses within the stimulation waveform. The one or more processors may be configured apply a deconvolution matrix to the evoked potential waveforms in order to derive the candidate response functions. The stimulation waveform may include a series of pulses defined based on a pseudorandom binary sequence. The compare operation may apply the pseudorandom binary sequence to the evoked potential waveforms in order to derive the candidate response functions.

BRIEF DESCRIPTION OF THE DRAWINGS

FIG. 4A illustrates an example of a stimulation waveform and related evoked responses waveform measured in connection there with in accordance with embodiments herein.

FIG. 7 illustrates a deconvolution matrix M (Equation 3) that may be utilized to perform deconvolution upon evoked potential (EP) waveforms to derive candidate response functions in accordance with embodiments herein.

DETAILED DESCRIPTION

Figure 1A:
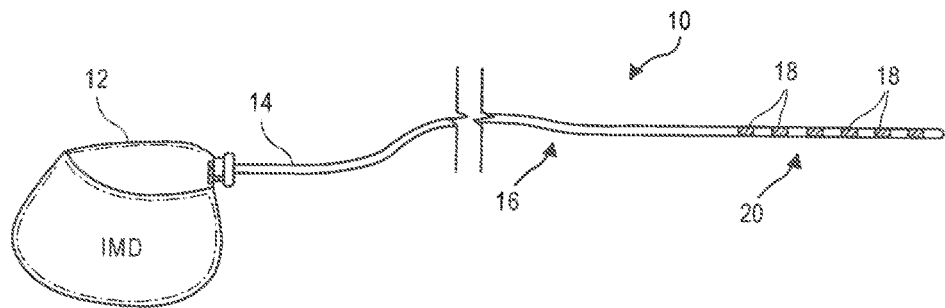
FIG. 1A illustrates example neurological stimulation (NS) systems for electrically stimulating a predetermined site area to treat one or more neurological disorders or conditions in accordance with embodiments herein.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Overview

Various embodiments described herein include a method and/or system to identify a neuronal system response to stimulation. The identification of the neuronal system response is used as a basis to select (e.g., optimize) stimulation parameters for neuromodulation systems. The stimulation parameters may be selected to define an input stimulation waveform in a patient-specific manner that may be adjusted over time. A stimulation waveform (e.g., a single excitation pulse or a randomized pulse train) is generated and associated evoked neural responses are recorded. An evoked potential or evoked response is an electrical potential recorded from the nervous system of a human or other animal following presentation of a stimulus, as distinct from spontaneous potentials as detected by electroencephalography (EEG), electromyography (EMG), or other electrophysiologic recording method.

The input stimulation waveform and evoked neural responses are compared, such as by measuring similarities and/or differences there between. For example, cross-correlation may be used to compare the stimulation waveform and the corresponding evoked response. The cross-correlation of the input stimulation waveform with the evoked response enables identification of the neuronal system response. Identification of the system response allows for selection of a desired values for (e.g., optimal) neurostimulation parameters, such as frequency, amplitude, pulse width, contact configuration, and/or duty cycle.

As described herein, a neuronal system response for a region of interest is described by one or a collection of response functions. Embodiments herein determined a collection of candidate response functions associated with a region of interest. From the candidate response functions, a resultant response function is determined based on various criteria. The collection of candidate response functions and the resultant response function separately or collectively defined the overall neuronal system response.

Example Applications

Embodiments herein have applications in various neural stimulation areas such as deep brain stimulation, spinal cord stimulation, cortical stimulation, and peripheral nerve stimulation. For example, in cortical stimulation for treatment of post-stroke rehabilitation, long-term alteration in the system response can be used to assess whether there are changes in synaptic connections that may be a prerequisite for clinical benefit. As another example, in DBS and cortical stimulation for treatment of epilepsy, embodiments, herein can be used to measure the brain's response to stimulation in the interictal (asymptomatic) state. Typically, programming stimulation settings for epilepsy is difficult, due to the rare occurrence of seizures needed to test clinical effectiveness. In accordance with embodiments herein, when the system response is known, stimulation parameters can be adjusted to those that promote alpha-wave LFPs (8-12 Hz) and sigma-wave LFPs (12-15 Hz), and avoid generation of delta-wave LFPs (0-4 Hz). A similar procedure could be used for tuning DBS parameters in both depression and movement disorders (e.g., Parkinson's disease, essential tremor, and dystonia).

An example of an application of embodiments herein relates to brain thalamic stimulation in order to create sensorimotor rhythm, such as to prevent epilepsy. Today, patients with drug refractory epilepsy have been trained using biofeedback to produce sensorimotor rhythm (e.g. 12 to 15 Hz EEG signal) that reduces seizures. However, conventional drug refractory training is time intensive and an imprecise therapy.

Figure 4B:
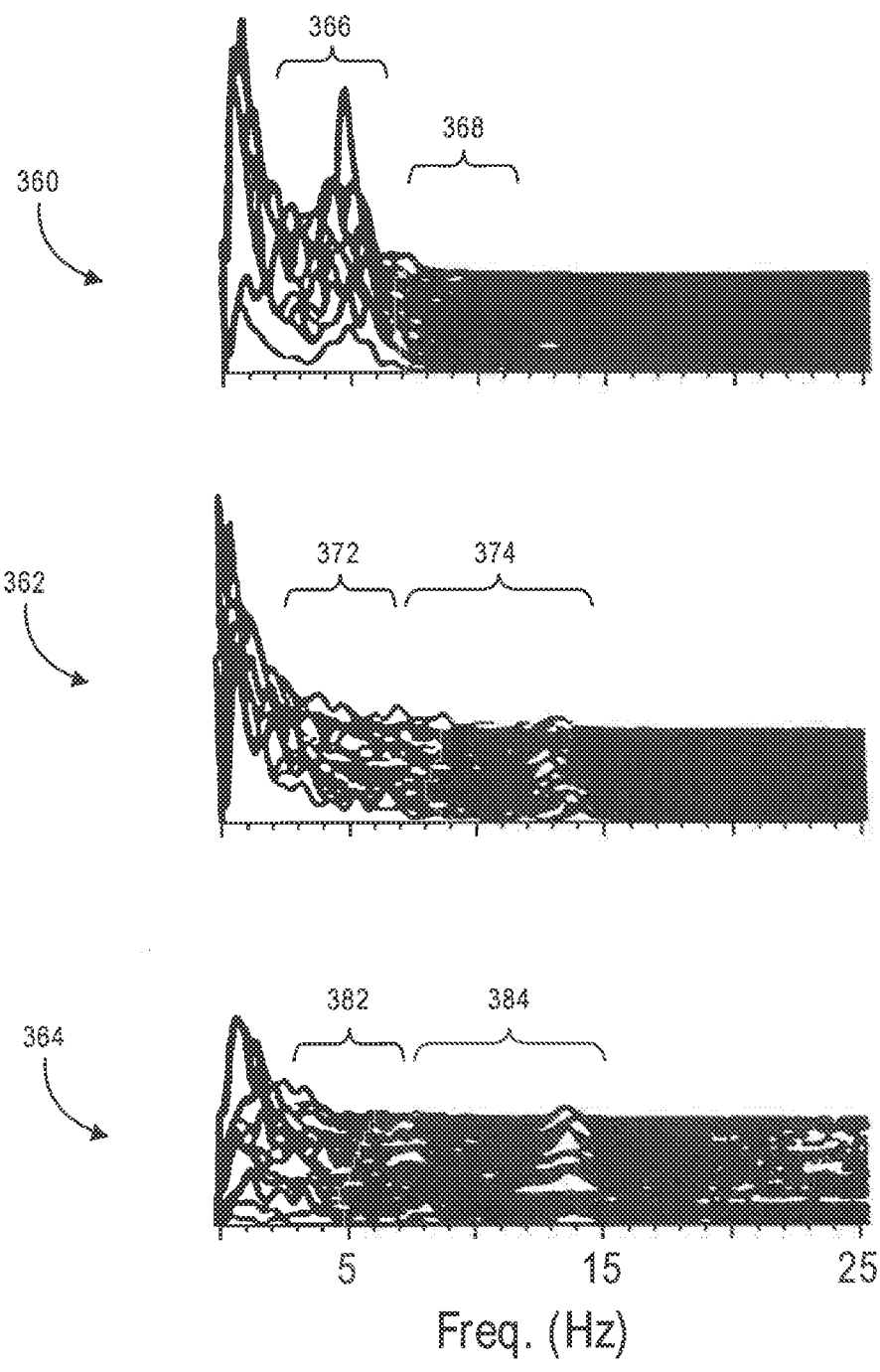
FIG. 4B illustrates graphs of compressed power spectral arrays that are measured by an electroencephalogram (EEG) during stage 2 sleep in an adult epileptic undergoing sensorimotor rhythm (SMR) feedback training twice weekly in accordance with embodiments herein.

FIG. 4B illustrates graphs of compressed power spectral arrays that are measured by an electroencephalogram (EEG) during stage 2 sleep in an adult epileptic undergoing sensorimotor rhythm (SMR) feedback training twice weekly. The graphs plot power (brain wave activity) along the vertical axis and brain wave frequency along the horizontal axis. Graph 360 corresponds to a patient's sleep behavior at the beginning of SMR feedback training, while graph 362 corresponds to the patient's sleep behavior after six weeks of SMR feedback training. Graph 364 illustrates the patient's sleep behavior after 18 weeks of SMR feedback training. Graphs 360, 362, and 364 depict power in respective frequency bands 366, 368, 372, 374, 382, and 384 for the various stages of the SMR feedback training.

As illustrated in graph 360, a pattern of brain wave activity peaks (denoted at 366) are exhibited in the 4-7 Hz frequency range (which represents an abnormally slow theta wave frequency range), while very little brain wave activity (denoted at 368) is exhibited in the 12-15 Hz frequency range (corresponding to sleep spindles or the sigma wave frequency range). A sleep spindle is a burst of oscillatory brain activity visible on an EEG that occurs during stage 2 sleep. The sleep spindle includes brain activity in the 12-14 Hz frequency range that occurs for at least 0.5 seconds. Sleep spindles are generated in the reticular nucleus of the thalamus.

Embodiments described herein locate one or more leads in a position proximate to a neuronal region of interest (ROI) in the brain in order to perform thalamic stimulation. In addition, the same lead or a different lead is positioned proximate to the brain neuronal ROI in order to perform cortical sensing. Excitation pulses are delivered and evoked responses are measured and analyzed in order to identify a patient specific neuronal system response. The neuronal system response is then utilized to determine neural stimulation parameter levels that achieve a desired (e.g. maximized) sensorimotor rhythm to reduce epileptic seizures. Embodiments herein define the neural stimulation parameter settings used to deliver excitation pulses, in connection with thalamic VPL nucleus stimulation, in order to enhance the EEG spindles within the 8 to 15 Hz frequency range at the sensorimotor cortex.

Optionally, embodiments herein may be implanted with alternative applications. For example, a system response may be determined for an ROI associated with sleep apnea. Stimulation parameters may be derived from the system response that are configured to provoke inspiration in central sleep apnea by altering neural control in the medulla oblongata and pons Varolli neuronal region of interest. For example, the neuronal system response may be determined by providing stimulation in the pre-Botzinger complex region and recording evoked potentials from the dorsal respiratory group. The evoked potentials may be then compared to the excitation pulses to derive response functions that characterize the neuronal system response. From the neuronal system response, neural stimulation parameters may be defined to suppress central sleep apnea.

As another example, embodiments may be implemented that measure intracortical inhibition in chronic neuropathic pain as feedback adjustment of spinal cord stimulation, dorsal root ganglia stimulation or cortical stimulation for pain.

As another example, embodiments may be implemented that stimulate an area such as Br25 or ventral capsule (VC) and/or ventral striatum (VS) in treatment refractory obsessive compulsive disorder (OCD). Embodiments may be implemented that stimulate areas in connection with various reward system disorders, impulsive behavior or attention deficit/hyperactivity disorder (ADHD). The system measures evoked responses to derive basal activity levels, such as in the nucleus accumbens or ventral tegmental area. Based on response functions between the excitation pulses and evoked responses, stimulation parameters may be defined to treat reward system disorders, impulse behaviors, OCD, ADHD and the like. As a further example, embodiments may be implemented to provide deep brain stimulation for various psychiatric disorders, such as the disorders described in the article "Deep Brain Stimulation for Psychiatric Disorders", by Holtzheimer, Mayberg, 2011, Annual Review of Neuroscience, Vol 34, pages 289-307, the complete subject matter of which is expressly incorporated by reference herein in its entirety.

As another example, embodiments may be implemented to detect altered output of medial globus pallidus to thalamic motor nuclei associated with Parkinson's disease or essential tremor and used to optimize DBS. As another example, embodiments may be implemented to enhance recovery in stroke patients by sensing in the contralateral cortex or lateral cortex and optimizing dorsal root stimulation, cortical stimulation, or SCS.

As another example, embodiments may be implemented that utilize an absence of a pathophysiologic neural pattern as an indicator of successful therapy.

Electrical Stimulation Devices

Figure 1B:
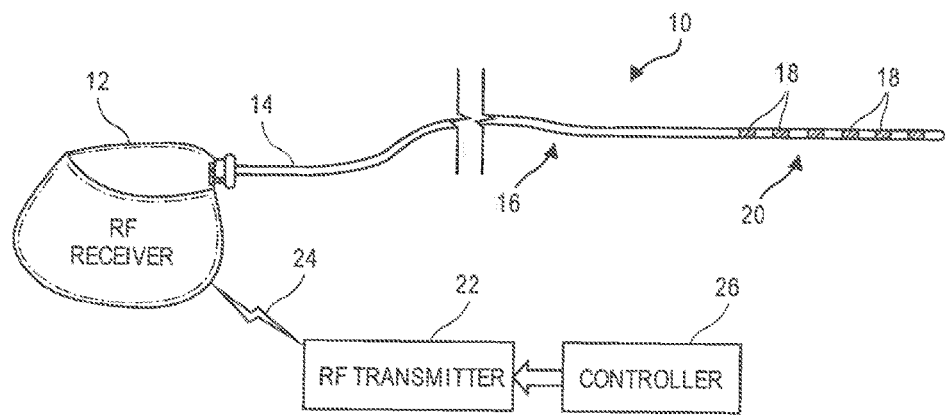
FIG. 1B illustrates example neurological stimulation (NS) systems for electrically stimulating a predetermined site area to treat one or more neurological disorders or conditions in accordance with embodiments herein.

FIGS. 1A-1B illustrate example neurological stimulation (NS) systems 10 for electrically stimulating a predetermined site area to treat one or more neurological disorders or conditions. In general terms, stimulation system 10 includes an implantable pulse generating source or electrical IMD 12 (generally referred to as an "implantable medical device" or "IMD") and one or more implantable electrodes or electrical stimulation leads 14 for applying stimulation pulses to a predetermined site. In operation, both of these primary components are implanted in the person's body, as discussed below. In certain embodiments, IMD 12 is coupled directly to a connecting portion 16 of stimulation lead 14. In other embodiments, IMD 12 is incorporated into the stimulation lead 14 and IMD 12 instead is embedded within stimulation lead 14. For example, such a stimulation system 10 may be a Bion® stimulation system manufactured by Advanced Bionics Corporation. Whether IMD 12 is coupled directly to or embedded within the stimulation lead 14, IMD 12 controls the stimulation pulses transmitted to one or more stimulation electrodes 18 located on a stimulating portion 20 of stimulation lead 14, positioned in communication with a predetermined site, according to suitable therapy parameters (e.g., duration, amplitude or intensity, frequency, pulse width, firing delay, etc.).

As contemplated in embodiments herein, a predetermined stimulation site of interest can include either peripheral neuronal tissue and/or central neuronal tissue. Neuronal tissue includes any tissue associated with the peripheral nervous system or the central nervous system. Peripheral neuronal tissue can include any neuronal tissue that lies outside the brain, brainstem or spinal cord. Peripheral nerves can include, but are not limited to olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves.

Central neuronal tissue includes brain tissue, spinal tissue or brainstem tissue. Brain tissue can include thalamus/subthalamus, basal ganglia, hippocampus, amygdala, hypothalamus, mammilary bodies, substantia nigra or cortex or white matter tracts afferent to or efferent from the above-mentioned brain tissue, inclusive of the corpus callosum. Spinal tissue can include the ascending and descending tracts of the spinal cord, more specifically, the ascending tracts of that comprise intralaminar neurons or the dorsal column. The brainstem tissue can include the medulla oblongata, pons or mesencephalon, more particular the posterior pons or posterior mesencephalon, Lushka's foramen, and ventrolateral part of the medulla oblongata.

In FIG. 1B, the IMD 12 includes an implantable wireless receiver. An example of a wireless receiver may be one manufactured by Advanced Neuromodulation Systems, Inc., such as the Renew® system, part numbers 3408 and 3416. The wireless receiver is capable of receiving wireless signals from a wireless transmitter 22 located external to the person's body. The wireless signals are represented in FIG. 1B by wireless link symbol 24. A doctor, the patient, or another user of IMD 12 may use a controller 26 located external to the person's body to provide control signals for operation of IMD 12. Controller 26 provides the control signals to wireless transmitter 22, wireless transmitter 22 transmits the control signals and power to the wireless receiver of IMD 12, and IMD 12 uses the control signals to vary the signal parameters of electrical signals transmitted through electrical stimulation lead 14 to the stimulation site. Thus, the external controller 26 can be for example, a handheld programmer, to provide a means for programming the IMD. An example wireless transmitter may be one manufactured by Advanced Neuromodulation Systems, Inc., such as the Renew® system, part numbers 3508 and 3516.

The IMD 12 includes a microprocessor and a pulse generation module. The pulse generation module generates the electrical pulses according to a defined pulse width, pulse amplitude and pulse-to-pulse interval, and applies the electrical pulses to defined electrodes (or electrode combinations). The microprocessor controls the operations of the pulse generation module according to program instructions stored in memory in the IMD 12.

The IMD 12 can be adapted by programming the microprocessor to deliver a number of pulses that are separated by an appropriate pulse-to-pulse interval. Optionally, when utilizing burst stimulation, the programming of the microprocessor may cause the pulse generation module to cease pulse generation operations for an interburst interval.

The microprocessor can be programmed to allow the various characteristics of the therapy to be set automatically or by a physician to allow the pulse trains to be customized for multiple particular pathologies of a patient. For example, the pulse amplitude, the interpulse interval, the interburst interval, the number of bursts to be repeated in succession, the electrode combinations, the firing delay between stimulation waveforms delivered to different electrode combinations, the amplitude of the recharging pulse, and other such characteristics could be controlled using respective parameters accessed by the microprocessor during burst stimulus operations. These parameters could be set to desired values by an external programming device via implementing the processes described herein.

In another embodiment, the IMD 12 can be implemented using a digital signal processor and one or several digital-to-analog converters. The stimulus waveform could be defined in memory and applied to a pulse generating circuit for application through electrodes of the medical lead. The digital signal processor could scale the various portions of the waveform output by the pulse generating circuit in amplitude and within the time domain (e.g., for the various intervals) according to the various parameters.

Figure 1C:
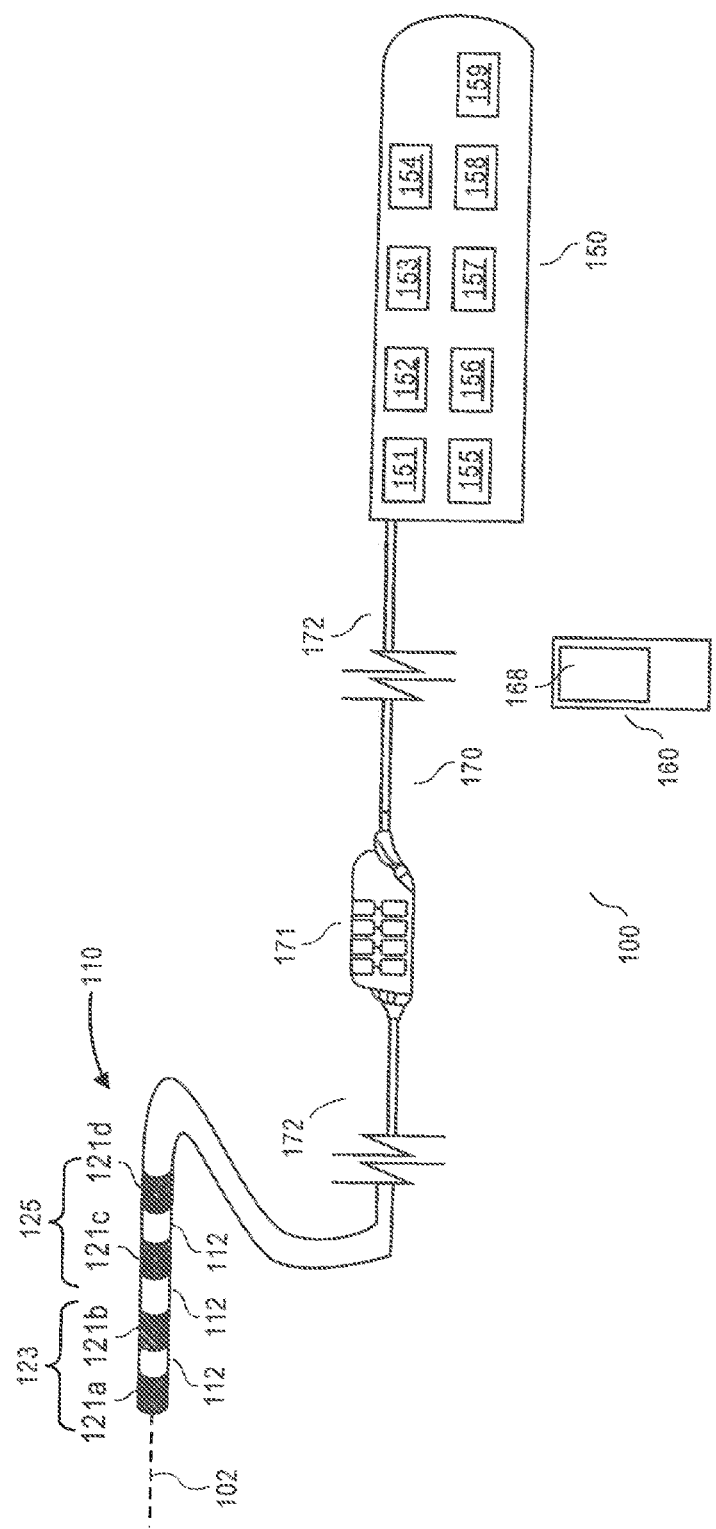
FIG. 1C depicts an NS system that delivers therapies to patient body parts in accordance with embodiments herein.
Figure 2A:
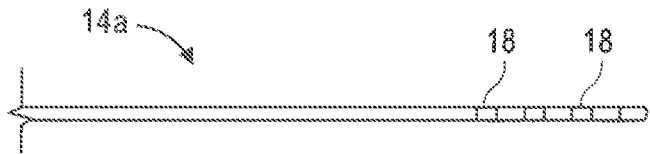
FIG. 2A illustrates example stimulation leads that may be used for electrically stimulating the predetermined site to treat one or more neurological disorders or conditions in accordance with embodiments herein.
Figure 2B:
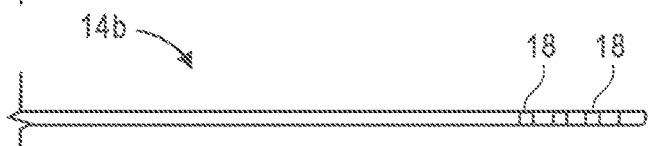
FIG. 2B illustrates example stimulation leads that may be used for electrically stimulating the predetermined site to treat one or more neurological disorders or conditions in accordance with embodiments herein.
Figure 2C:
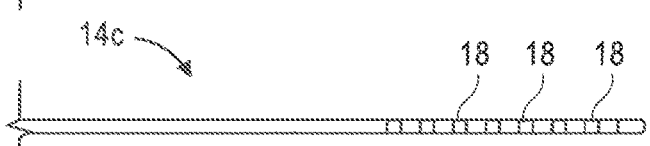
FIG. 2C illustrates example stimulation leads that may be used for electrically stimulating the predetermined site to treat one or more neurological disorders or conditions in accordance with embodiments herein.
Figure 2D:
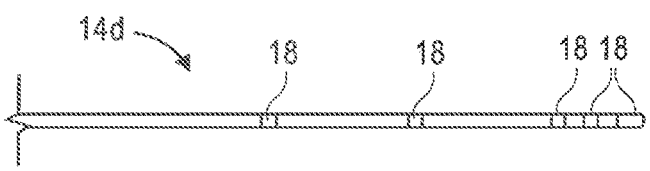
FIG. 2D illustrates example stimulation leads that may be used for electrically stimulating the predetermined site to treat one or more neurological disorders or conditions in accordance with embodiments herein.
Figure 2E:
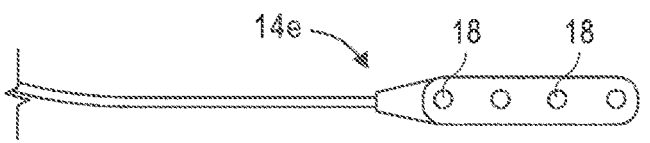
FIG. 2E illustrates example stimulation leads that may be used for electrically stimulating the predetermined site to treat one or more neurological disorders or conditions in accordance with embodiments herein.
Figure 2F:
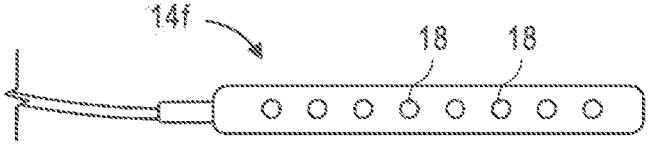
FIG. 2F illustrates example stimulation leads that may be used for electrically stimulating the predetermined site to treat one or more neurological disorders or conditions in accordance with embodiments herein.
Figure 2G:
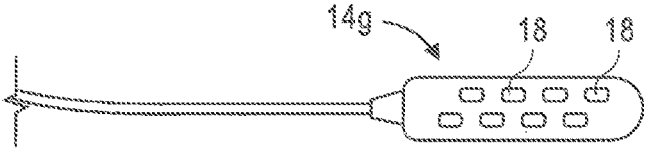
FIG. 2G illustrates example stimulation leads that may be used for electrically stimulating the predetermined site to treat one or more neurological disorders or conditions in accordance with embodiments herein.
Figure 2H:
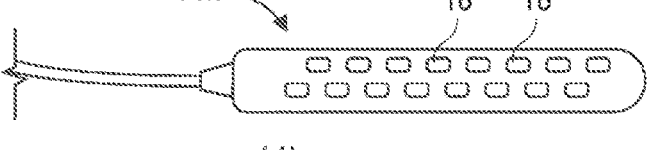
FIG. 2H illustrates example stimulation leads that may be used for electrically stimulating the predetermined site to treat one or more neurological disorders or conditions in accordance with embodiments herein.
Figure 2I:
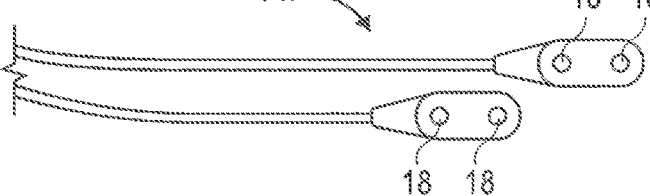
FIG. 2I illustrates example stimulation leads that may be used for electrically stimulating the predetermined site to treat one or more neurological disorders or conditions in accordance with embodiments herein.

FIG. 1C depicts an NS system 100 that delivers therapies to patient body parts (through corresponding portions of the nerve tissue). For example, the NS system 100 may be adapted to stimulate spinal cord tissue, peripheral nervous tissue, deep brain tissue, and/or any other suitable nervous/brain tissue of interest within a patient's body. The NS system 100 may be controlled to deliver various types of stimulation therapy, such as multiple different tonic neurostimulation therapies, burst neurostimulation therapies and the like. Burst neurostimulation includes short sequences of monophasic or biphasic pulses, where each sequence is separated by a quiescent period.

The NS system 100 delivers NS therapy based on a preprogrammed sequence. The therapy parameters of the sequence may include, among other things, pulse amplitude, pulse polarity, pulse width, pulse frequency, interpulse interval, inter burst interval, electrode combinations, firing delay and the like. Optionally, the NS system 100 may represent a closed loop neurostimulation device that is configured to provide real-time sensing functions from a lead. The configuration of the lead sensing electrodes may be varied depending on the neuronal anatomy of the sensing site(s) of interest. The size and shape of electrodes is varied based on the implant location. The electronic components within the NS system 100 are designed with both stimulation and sensing capabilities, including alternative stimulation therapy, such as burst mode and the like.

The NS system 100 includes an implantable medical device (IMD) 150 that is adapted to generate electrical pulses for application to tissue of a patient. The IMD 150 typically comprises a metallic housing or can 44 that enclose a controller 151, pulse generating circuit 152, a charge storage circuit 153, a battery 154, a far-field and/or near field communication circuit 155, battery charging circuit 156, switching circuit 157, memory 158 and the like. The charge storage circuit 153 may represent one or more capacitors and/or battery cells that store charge used to produce the therapies described herein. The pulse generating circuit 152, under control of the controller 151, manages discharge of the charge storage circuit 153 to generate the stimulation waveform (shape the morphology of the waveform) delivered while discharging energy. The switching circuit 157 connects select combinations of the electrodes 121a-d to the pulse generating circuit 152 thereby directing the stimulation waveform to a desired electrode combination. By way of example, the switching circuit 157 may include one or more multiplexer circuits connected between the output of the pulse generating circuit and the electrodes. As explained herein, the switching circuit 157 successively connects the pulse generating circuit 152 to successive electrode combinations 123 and 125. The components 151-158 are also within the IMD 12 (FIGS. 1A and 1B). The IMD 150 also includes one or more EP sensing circuits 159 that are configured to measure EP waveforms from a select combination of electrodes. For example, the EP sensing circuit 159 may include one or more separate circuits connected, through the switching circuit 157, to desired combinations of electrodes. The sensing circuits 159 may include amplifiers, low pass filters, band pass filters, high pass filters, A/D converters and the like to identify the EP waveform within signals sensed by the electrodes. The internal components of the sensing circuits 159 may vary based on the nature of the EP waveform that is being measured. For example, the sensing circuit 159 may be constructed to measure neuronal activity that includes an impulse response that is generated in response to each stimulus pulse, wherein the evoked response is superimposed on an underlying, intrinsic low frequency signal.

The controller 151 typically includes one or more processors, such as a microcontroller, for controlling the various other components of the device. Software code is typically stored in memory of the IMD 150 for execution by the microcontroller or processor to control the various components of the device.

The IMD 150 may comprise a separate or an attached extension component 170. If the extension component 170 is a separate component, the extension component 170 may connect with the "header" portion of the IMD 150 as is known in the art. If the extension component 170 is integrated with the IMD 150, internal electrical connections may be made through respective conductive components. Within the IMD 150, electrical pulses are generated by the pulse generating circuit 152 and are provided to the switching circuit 157. The switching circuit 157 connects to outputs of the IMD 150. Electrical connectors (e.g., "Bal-Seal" connectors) within the connector portion 171 of the extension component 170 or within the IMD header may be employed to conduct various stimulation pulses. The terminals of one or more leads 110 are inserted within connector portion 171 or within the IMD header for electrical connection with respective connectors. Thereby, the pulses originating from the IMD 150 are provided to the lead 110. The pulses are then conducted through the conductors of the lead 110 and applied to tissue of a patient via stimulation electrodes 121a-d that are coupled to blocking capacitors. Any suitable known or later developed design may be employed for connector portion 171.

The stimulation electrodes 121a-d may be positioned along a horizontal axis 102 of the lead 110, and are angularly positioned about the horizontal axis 102 so the stimulation electrodes 121a-d do not overlap. The stimulation electrodes 121a-d may be in the shape of a ring such that each stimulation electrode 121a-d continuously covers the circumference of the exterior surface of the lead 110. Adjacent stimulation electrodes 121a-d are separated from one another by non-conducting rings 112, which electrically isolate each stimulation electrode 121a-d from an adjacent stimulation electrode 121a-d. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 121a-d may be configured to emit the pulses in an outward radial direction proximate to or within a stimulation target. Additionally or alternatively, the stimulation electrodes 121a-d may be in the shape of a split or non-continuous ring such that the pulse may be directed in an outward radial direction adjacent to the stimulation electrodes 121a-d. Additionally or alternatively, paddle leads may be utilized with an array of electrodes thereon. The stimulation electrodes 121a-d delivers tonic, high frequency and/or burst stimulation waveforms. It is recognized that other waveforms may be utilized. Optionally, the electrodes 121a-d may also sense neural oscillations and/or sensory action potential (neural oscillation signals) for a data collection window.

The lead 110 may comprise a lead body 172 of insulative material about a plurality of conductors within the material that extend from a proximal end of lead 110, proximate to the IMD 150, to its distal end. The conductors electrically couple a plurality of the stimulation electrodes 121 to a plurality of terminals (not shown) of the lead 110. The terminals are adapted to receive electrical pulses and the stimulation electrodes 121a-d are adapted to apply the pulses to the stimulation target of the patient. Also, sensing of physiological signals may occur through the electrodes 121a-d, the conductors, and the terminals. It should be noted that although the lead 110 is depicted with four stimulation electrodes 121a-d, the lead 110 may include any suitable number of stimulation electrodes 121a-d (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

By way of example, the IMD 12, 150 may include a processor and associated charge control circuit as described in U.S. Pat. No. 7,571,007, entitled "SYSTEMS AND METHODS FOR USE IN PULSE GENERATION," which is expressly incorporated herein by reference. Circuits for recharging a rechargeable battery (e.g., battery charging circuit 156) of an IMD using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference. An example and discussion of "constant current" pulse generating circuit (e.g., pulse generating circuit 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuit may be provided within the IMD 12, 150. Different burst and/or tonic pulses on different stimulation electrodes may be generated using a single pulse generating circuit using consecutively generated pulses. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of pulse generating circuit may be employed to provide a greater number of component sequences (e.g., one PG to produce two tonic stimulation waveforms and one PG to produce a burst stimulation waveform) that include generated and delivered stimulation pulses through various stimulation electrodes of one or more leads. Although constant current pulse generating circuit is contemplated for some embodiments, any other suitable type of pulse generating circuit may be employed such as constant voltage pulse generating circuit.

The controller 151 delivers the stimulation waveform to an electrode combination located proximate to nervous tissue of interest. Memory 158 stores software to control operation of the controller 151. The memory 158 also stores neural oscillation signals, therapy parameters, neural oscillation activity level data, sensation scales and the like. For example, the memory 158 may save neural oscillation activity level data for various different therapies as applied over a short or extended period of time.

An external device 160 may be implemented to charge/recharge the battery 154 of the IMD 150 (although a separate recharging device could alternatively be employed) and to program the IMD 150 on the pulse specifications while implanted within the patient. The external device 160 may represent physician programmer device, a personal computer, workstation, server, laptop computer, table device, smart phone and the like. Although, in alternative embodiments separate programmer devices may be employed for charging and/or programming the NS system 100. The external device 160 may be a processor-based system that possesses wireless communication capabilities. Software may be stored within a non-transitory memory of the external device 160, which may be executed by the processor to control the various operations of the external device 160. The external device 160 communicates with the IMD 150 utilizing a wireless communications protocol, such as the Bluetooth protocol and the like.

Alternatively or additionally, a "wand" (not shown) may be electrically connected to the external device 160 through suitable electrical connectors (not shown). The wand may include a telemetry component (e.g., inductor coil, RF transceiver) (not shown) that allows bi-directional communication with the IMD 150.

The external device 160 preferably provides one or more user interfaces 168 (e.g., touchscreen, keyboard, mouse, buttons, or the like) allowing the user to operate the IMD 150. The external device 160 may be controlled by the user (e.g., doctor, clinician) through the user interface 168 allowing the user to interact with the IMD 150. The user interface 168 may permit the user to move electrical stimulation along and/or across one or more of the lead(s) 110 using different stimulation electrode 121 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference.

Also, the external device 160 may permit operation of the IMD 12, 150 by loading one or more NS therapies to treat the patient. Each NS therapy is defined by one or more sets of stimulation parameters, including pulse amplitude, pulse width, pulse frequency or interpulse period, firing delay, pulse repetition parameter (e.g., number of times for a given pulse to be repeated for respective stimset during execution of program), biphasic pulses, monophasic pulses, etc. The IMD 150 modifies its internal parameters in response to the control signals from the external device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

FIGS. 2A-2I illustrate example stimulation leads 14 that may be used for electrically stimulating the predetermined site to treat one or more neurological disorders or conditions. As described above, each of the one or more stimulation leads 14 incorporated in stimulation systems 10, 100 includes one or more stimulation electrodes 18 adapted to be positioned in communication with the predetermined site and used to deliver the stimulation pulses received from IMD 12 (or pulse generating circuit 157 in FIG. 1C). A percutaneous stimulation lead 14 (corresponding to the lead 110 in FIG. 1C), such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (e.g., generally perpendicular to the axis of stimulation lead 14) in all directions. A laminotomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. Although various types of stimulation leads 14 are shown as examples, embodiments herein contemplate stimulation system 10 including any suitable type of stimulation lead 14 in any suitable number. In addition, stimulation leads 14 may be used alone or in combination. For example, medial or unilateral stimulation of the predetermined site may be accomplished using a single electrical stimulation lead 14 implanted in communication with the predetermined site in one side of the head, while bilateral electrical stimulation of the predetermined site may be accomplished using two stimulation leads 14 implanted in communication with the predetermined site in opposite sides of the head.

In one embodiment, the stimulation source is transcutaneously in communication with the electrical stimulation lead. In "transcutaneous" electrical nerve stimulation (TENS), the stimulation source is external to the patient's body, and may be worn in an appropriate fanny pack or belt, and the electrical stimulation lead is in communication with the stimulation source, either remotely or directly. In another embodiment, the stimulation is percutaneous. In "percutaneous" electrical nerve stimulation (PENS), needles are inserted to an appropriate depth around or immediately adjacent to a predetermined stimulation site, and then stimulated.

The IMD 12, 150 allow each electrode of each lead to be defined as a positive, a negative, or a neutral polarity. For each electrode combination (e.g., the defined polarity of at least two electrodes having at least one cathode and at least one anode), an electrical signal can have at least a definable amplitude (e.g., voltage), pulse width, and frequency, where these variables may be independently adjusted to finely select the sensory transmitting brain tissue required to inhibit transmission of neuronal signals. Generally, amplitudes, pulse widths, and frequencies are determinable by the capabilities of the neurostimulation systems, which are known by those of skill in the art. Voltages that may be used can include, for example about 0.5 to about 10 volts, more preferably about 1 to about 10 volts.

It is envisaged that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

FIGS. 2A-2I respectively depict stimulation portions for inclusion at the distal end of lead. Stimulation portion depicts a conventional stimulation portion of a "percutaneous" lead with multiple ring electrodes. Stimulation portion depicts a stimulation portion including several segmented electrodes. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion includes multiple planar electrodes on a paddle structure.

Method for Determining Neuronal System Response

Figure 3A:
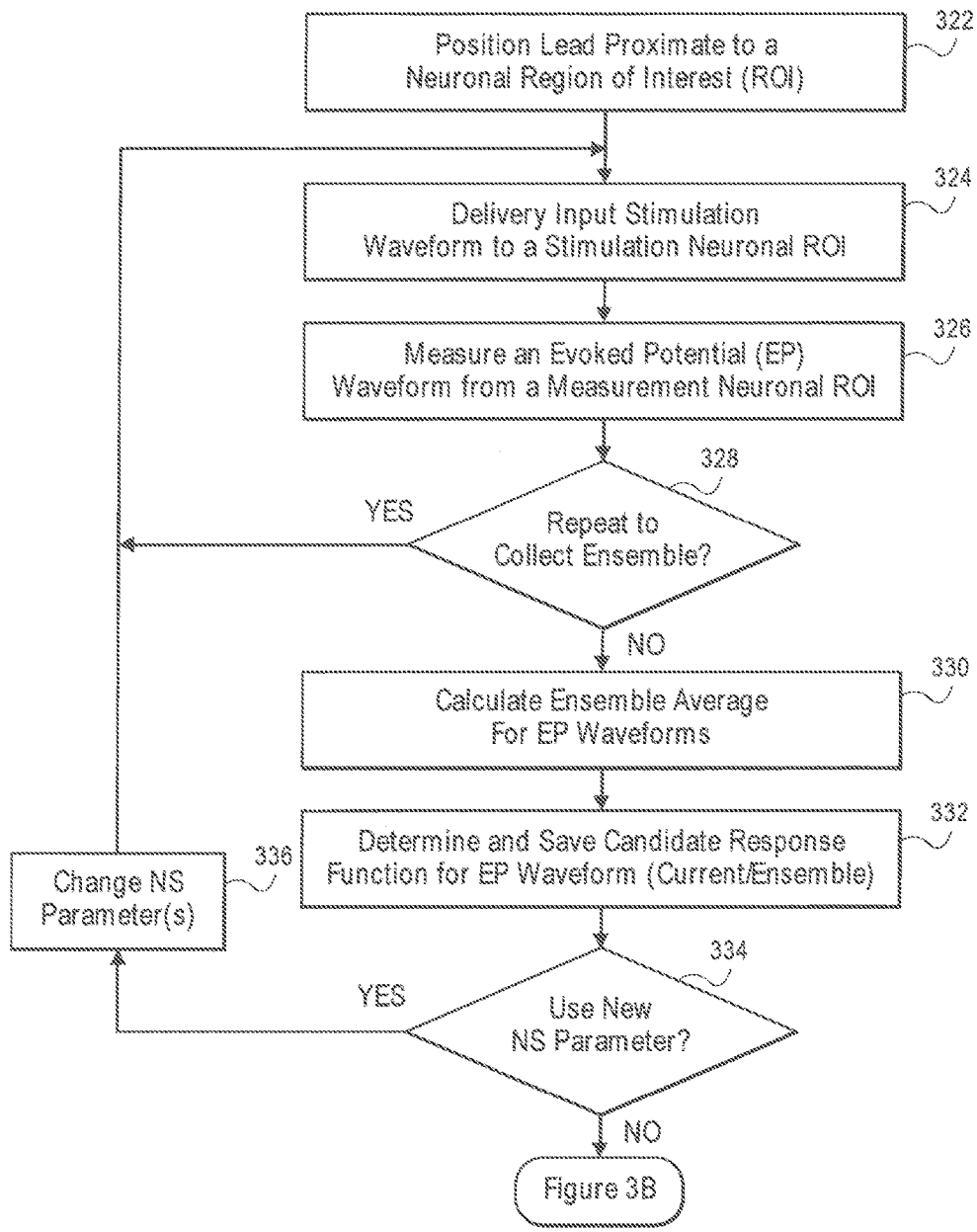
FIG. 3A is a flowchart of a method for determining neuronal system response based on a relation between excitation pulses and evoked potential waveforms in accordance with embodiments herein.

FIG. 3A is a flowchart of a method for determining neuronal system response based on a relation between excitation pulses and evoked potential waveforms. The method may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

Beginning at 322, one or more leads are positioned proximate to one or more neuronal ROI. The lead(s) include electrodes arranged in a one or two dimensional electrode array that is configured to perform one or both of delivering excitation pulses and measuring evoked responses. As one example, a single lead may be implanted at a desired position. A first set of electrodes on the lead are configured to deliver excitation pulses, while a second set of electrodes on the same lead are configured to measure evoked responses. Alternatively, more than one lead may be implanted with all or a portion of the electrodes on one lead configured to deliver excitation pulses and all or a portion of the electrodes on another lead configured to measure evoked responses. Additionally or alternatively, electrodes on multiple leads may perform one or both of delivery of excitation pulses and measurement of evoked responses. Continuing with the foregoing examples, different electrodes may be used for stimulation and for measuring EP waveforms when at least partially different regions of the neuronal ROI are designated for stimulation and for measuring EP waveforms. For example, a first region of the ROI may be designated to receive stimulation and a second region may be designated for measuring EP waveforms. The first and second regions may be mutually exclusive, partially overlapping or entirely overlapping.

As noted herein, one exemplary implementation may be in connection with providing brain thalamic stimulation to create sensorimotor rhythms to prevent epileptic seizures. In the present example, one or more leads are positioned with electrodes in a desired position to perform cortical sensing and with electrodes to perform cortical or deep brain (e.g., ventral posterolateral) stimulation.

As another example, a lead may be positioned at a target position within an epidural space of a patient so as to be in close proximity to a neuronal ROI along the dorsal column (DC). The lead includes a plurality of electrodes that may form one or more series of electrodes overlaid on the surface of the lead. All or a portion of the electrodes may be positioned proximate and/or adjacent to a dura layer of the DC. The electrodes are electrically coupled to an IPG. Optionally, a second series of electrodes on the lead may be proximate to and/or adjacent to the epidural space of the dorsal root (DR). For example, the electrode may be located immediately adjacent to the DR. The DR may correspond to a particular or select dermatome to be stimulated by the IPG. The second series of electrodes are electrically coupled to the sensing circuitry of the IPG.

At 324, the NS system delivers a stimulation waveform that includes one or more excitation pulses. For example, an implantable pulse generator may deliver the stimulation waveform. Additionally or alternatively, an external pulse generator may deliver the stimulation waveform. The stimulation waveform is delivered to one or more electrodes in connection with delivering the excitation pulses to a stimulation region of the neuronal ROI. The stimulation waveform includes one or more excitation pulses that are defined based on predetermined neural stimulation parameters. The stimulation region of the neuronal ROI may be the same or a different region of the neuronal ROI for which EP waveforms are to be measured.

At 326, one or more processors of the NS system manage measurement and recording of an evoked response waveform from one or more electrodes to a measurement region of the neuronal ROI. The electrodes, measuring the evoked response waveform (also referred to as sensing electrodes), may represent the same electrodes used to deliver the excitation pulses (also referred to as stimulation electrodes). Additionally or alternatively, the sensing electrodes may be separate and distinct from the stimulation electrodes. Optionally, the sensing electrodes may be provided on the same or a separate lead relative to the stimulation electrodes. The evoked response waveform is collected by the neural stimulation system for a predetermined measurement window. The predetermined measurement window begins a predetermined lagging period of time following the beginning and/or end of the stimulation waveform.

The delivery of the stimulation waveform and recording of the EP waveform may be performed at the same site or distinct sites within the neuronal ROI. For example, in SCS, stimulation may be delivered at a site that provides pain relief for a patient, and EP waveforms may be recorded at a distant location along the spinal cord (e.g., towards the head), or somewhere within the brain. Alternatively, in DBS, stimulation may be delivered within one nucleus (e.g., STN for Parkinson's disease) and EP waveforms may be recorded at a distinct nucleus or brain region (e.g. cortex).

At 328, the one or more processors determine whether to repeat the operations at 324-326 with the same stimulation waveform. If so, flow returns to 324 in order to obtain additional EP waveforms (data points) associated with the same stimulation waveform. The operations at 324-326 are repeated a select number of times for a single common stimulation waveform in order to obtain an ensemble of evoked potential waveforms associated with a single stimulation waveform. As one example, the operations at 324-326 may be repeated 3 to 100 times in connection with a single common stimulation waveform. Optionally, the decision at 328 may be omitted entirely and instead the method may collect a single evoked potential waveform in connection with any one stimulation waveform. Once the ensemble of evoked potential waveforms is collected, flow moves to 330.

At 330, the one or more processors calculate an ensemble average of the EP waveforms associated with a current stimulation waveform. For example, EP waveforms may be aligned according to a common trigger point (e.g., the start of a stimulus pulse), and then combined to form an EP waveform ensemble, such as through averaging or some other mathematical operation. By collecting ensemble averages of EP waveforms in connection with a single set of neural stimulation parameters, embodiments herein provide substantial noise cancellation. The noise cancellation allows the methods and systems described herein to record small amplitude evoked responses and determine system responses based thereon. The small amplitude evoked responses may occur at neuronal regions of interest that are located remote from sensing electrodes, thereby affording greater sensitivity and specificity in connection with sensing EP waveforms corresponding to activity of interest.

At 332, one or more processors of the neural stimulation system compare an excitation pulse or pulses within the stimulation waveform with the ensemble average of the evoked response waveforms to obtain a candidate response function. Additionally or alternatively, at 332, one or more processors of the neural stimulation system compare an excitation pulse or pulses within the stimulation waveform with a raw evoked response waveform to obtain the candidate response function.

Additionally or alternatively, at 326-330, a series of stimulation pulses and the evoked response waveforms responsive to the series of stimulation pulses may be stored individually in their entirely without averaging or otherwise being combined. At 332, the one or more processors may compare the series of excitation pulses (pulse train) with the corresponding resultant series of evoked response waveforms to obtain the candidate response function.

The candidate response function is saved in a memory (e.g., within the neural stimulation system). As one example, the candidate response function represents a measure of a similarity of the excitation pulse(s) and EP waveform ensemble average as a function of a lag of the EP waveform ensemble average relative to the excitation pulse(s). For example, the comparing operation comprises performing a cross correlation analysis between the excitation pulse(s) and the EP waveform ensemble average to obtain the relation there between. Examples of cross correlation analysis and alternative analysis for determining response functions are described herein.

The stimulation waveforms may be tailored to have a causal link with the neural response (measured as an EP waveform). The stimulation waveforms are also configured to produce EP waveforms that are finite in duration, and do not continue indefinitely. The calculation at 332 performs a cross-correlation that utilizes only a finite portion of the EP waveform.

At 334, the one or more processors determine whether stimulation parameters should be adjusted, additional stimulation waveforms should be delivered, and corresponding EP waveform ensemble averages collected. If so, flow moves to 336. Otherwise, flow moves to the operations of FIG. 3B. At 336, the one or more processors changes one or more neural stimulation parameters that define the stimulation waveform. Various neural stimulation parameters are described herein that may be adjusted. For example, during each iteration through the change at 336 the system may incrementally step through a series of pulse amplitudes, while maintaining other stimulation parameters constant. For example, during a first group of iterations through the operations at 324-336, the pulse amplitude may be adjusted successively by a predetermined amount while maintaining a constant pulse width. During a second group of iterations through the operations at 324-336, the same group of pulse amplitudes may be used, but with a different constant pulse width. Similarly, various combinations of pulse amplitude, pulse width, duty cycle, frequency and electrode configurations may be utilized during each iteration through the operations at 324-336 to collect a corresponding number of ensemble averages of EP waveforms.

As another example, during one iteration the stimulation waveform may consist of a single excitation pulse. During another iteration, the stimulation waveform may comprise a series of pulses (e.g., FIG. 5).

At 334, the one or more processors determine when the method has obtained a sufficient collection of candidate response functions. When the desired number of candidate response functions are collected, no additional NS parameters are tested, and flow moves to FIG. 3B.

Figure 3B:
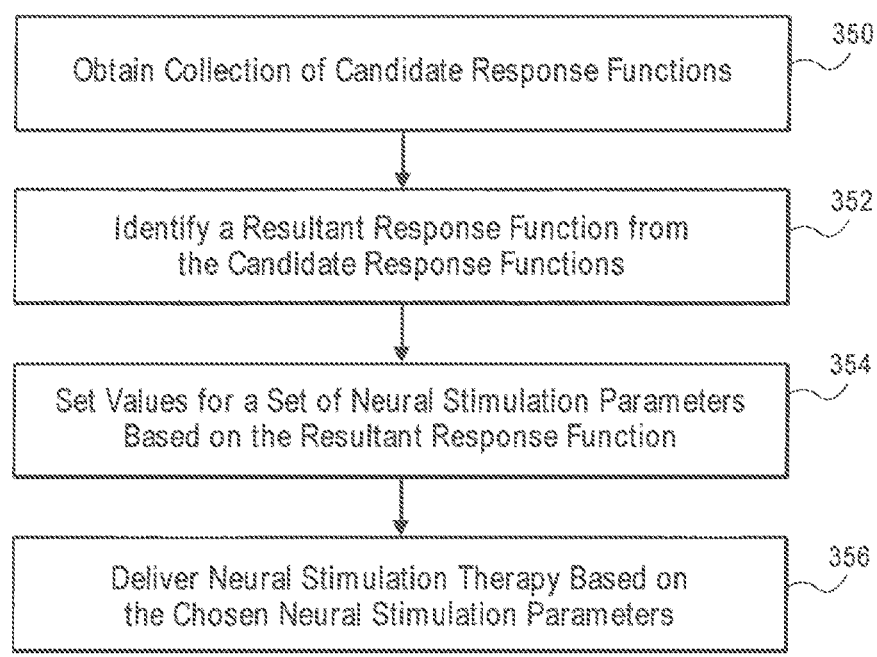
FIG. 3B illustrates a process for identifying a neuronal system response of interest and determining values for neural stimulation parameters in accordance with an embodiment herein.

FIG. 3B illustrates a process for identifying a neuronal system response of interest and determining values for neural stimulation parameters in accordance with an embodiment herein. At 350, one or more processors of neural stimulation system access the collection of candidate response functions. For example, a separate candidate response function may be saved in memory in connection with each set of values for the neural stimulation parameters. As a further example, when the neural stimulation parameters are adjusted to test 10 different pulse widths, each of which is utilized with five different pulse amplitudes, the resulting test would yield 50 different input stimulation waveforms. Each of the 50 different input stimulation waveforms may be delivered once. In response thereto a single EP waveform is collected and a corresponding candidate response function is determined after performing cross correlation between each single input stimulation waveform and corresponding EP waveform. Optionally, the response function may be determined by performing a deconvolution upon the EP waveform.

Continuing with the present example, each of the 50 different input stimulation waveforms may be delivered multiple times (e.g. 3-100 times), in order to derive an ensemble of EP waveforms in connection with each individual input stimulation waveform. When utilizing ensemble averaging, 50 different EP waveform ensemble averages would be collected, with each EP waveform ensemble average corresponding to a different combination of pulse width and pulse amplitude for the neural stimulation parameters.

At 352, the one or more processors identifies one of the candidate response functions as a resultant response function. The resultant response function corresponds to, and represents, the neuronal system response. The resultant response function may be identified from the candidate response functions based on various criteria. As explained herein, in connection with FIGS. 8A-8C, response functions may exhibit different characteristics of interest. One or more of the characteristics of interest may be utilized to select the resultant response function. Examples of characteristics of interest include, but are not limited to, i) initial and final response magnitude, ii) a shape of the response function, iii) rise time and/or falling time for all or a portion of a response function, iv) a duration of a local peak in the response function, v) a time interval over which the response function changes from maximum to minimum values and/or from minimum to maximum values, and the like. As other example characteristics, it may be desirable for the response function to include a single local peak, not multiple local peaks. Additionally or alternatively, a resultant response function may be selected as the candidate response function that exceeds a threshold within a desired portion of the response function (e.g. the starting point, an intermediate point, or the trailing tail).

At 354, the one or more processors determines, from the resultant response function, values for a set of neural stimulation parameters to be utilized when delivering an NS therapy to a patient. The set of neural stimulation parameters to be used with a neural stimulation therapy may be defined automatically based on the resultant response function. For example, the values for the set of neural stimulation parameters may be set to correspond to the input stimulation waveform delivered in connection with the resultant response function. As explained in connection with FIG. 3A, each candidate response function is derived from a comparison of a stimulation waveform and an EP waveform. At 354, the input stimulation waveform associated with the resultant response waveform may be identified and utilized to define the neural stimulation therapy.

Additionally or alternatively, the morphology of the resultant response function may be analyzed to identify values for the neural stimulation parameters of the neural stimulation therapy.

An example of a neuronal system response may be $h(t)=\exp(-t/\tau)u(t)$. In the present example, the neural stimulation therapy may use a regular, continuous stimulation waveform. Based on the foregoing example neuronal system response, the process may automatically determine to set the stimulation frequency at $F=1/\tau$. A stimulation frequency of $F=1/\tau$ may afford a desired level of masking for pathological activity. Knowledge of the system response may be useful for selecting a stimulation amplitude, pulse width, and/or contact configuration that recruit a sufficient number of targeted neurons.

As one example, the set of values for the neuro stimulation parameters may be set to define a therapy waveform that represents the inverse of the resultant response function. For example, when the resultant response function is defined to be h(t), the values for the neuro stimulation parameters may be set to be $x(t)/h(t)$, where x(t) represents a base therapy that is desired to be delivered. The base therapy is combined with an inverse of the resultant response function. Additionally or alternatively, the resultant response function may be combined with a base therapy in accordance with other mathematical operations (e.g., multiplication, addition, subtraction, convolution, conjugates, etc.)

Additionally or alternatively, templates may be defined for potential response functions. At 354, the resultant response function may be compared to one or more template response functions. Each template response function may have a corresponding set of values for the neural stimulation parameters associated with a neural stimulation therapy.

For example, the neuronal system response may have a response function that exhibits a shape corresponding to one of a number of predetermined templates.

In accordance with embodiments herein, the characteristics of interest in the response function may vary based on whether the system response indicates under recruitment or over recruitment of neurons in the region of interest. The characteristics of the system response may be different with under- or over-recruitment of neurons, compared to an optimal extent of neuronal recruitment.

In accordance with embodiments herein, neuronal regions of interest may exhibit a carry-over effect, whereby a desirable effect may continue to occur, even after a stimulation waveform has been discontinued for a period of time. A carry-over effect following stimulation, may be indicated in the response function, in which case, the system may adjust the duty cycle to a desired level (e.g. optimal duty cycle) that maintains clinical benefit while minimizing power consumption. For example, it may be determined that a satisfactory duty cycle delivers therapy for a 10 second period of time and discontinue therapy for a 10 second period of time. As an example, the stimulation may be discontinued for approximately the same amount of time as the carry-over effect. The response function assessments can be made periodically or following some external trigger, and will aid in identifying if the stimulation settings should be changed.

Optionally, the values for the neural stimulation parameters may be set by a physician or technician. For example, the resultant response function may be displayed to the user, who then sets the neural stimulation parameters in a manner to achieve a desired therapy. Additionally or alternatively, when presenting the resultant response function to a user, the system may present suggested values for the neural stimulation parameters and afford the user the option to accept or modify the suggested neural stimulation parameters.

At 356, the neural stimulation system begins delivering a neural stimulation therapy based on the neural stimulation parameters defined at 354.

The operations of one or both of FIGS. 3A and 3B may be performed at the time of implant. Optionally, the operations of one or both of FIGS. 3A and 3B may be performed periodically throughout operation. For example, the operations may be repeated at a predetermined periodic basis. Additionally or alternatively, the operations may be performed when certain criteria arise. For example, when a therapy is intended to prevent a particular behavior or disorder, the IMD may monitor one or more characteristics of the behavior or disorder. When the IMD delivers a successful therapy, the characteristic of the behavior/disorder may remain within a predetermined limit. However, when the IMD is no longer achieving a desired result, the characteristic of the behavior/disorder may exceed the predetermined limit. In accordance with embodiments herein, when the characteristic of the behavior or disorder exceeds the predetermined limit, the neural stimulation system may repeat the operations of FIGS. 3A and 3B to determine whether adjustments in the neural stimulation parameters are warranted. Optionally, a patient, physician, technician or other authorized individual may instruct the neural stimulation system to repeat the operations of FIGS. 3A and 3B, such as through a wireless communication with an external device.

Optionally, the operations of FIG. 3A may be performed independently from and on a different basis or periodic nature from the operations of FIG. 3B. Optionally, the operations of FIG. 3A may be performed by one neural stimulation device, while the operations of FIG. 3B are performed by a different device. For example, an implantable neural stimulation system may perform the operations of FIG. 3A, while an external device may perform the operations 350-354 of FIG. 3B, while the implantable neural stimulation system performs the therapy delivery operation at 356. As a further example of a manner in which the operations of FIGS. 3A and 3B may be distributed, an external device may perform each of the calculating and determining operations (e.g. 330, 332 and 336 in FIG. 3A, and 350-354 in FIG. 3B). An implantable neural stimulation system may perform the operations for delivering stimulation waveforms and measuring EP waveforms (e.g. 324-328 in FIG. 3A and 356 in FIG. 3B).

FIG. 4A illustrates an example of a stimulation waveform and related evoked responses waveform measured in connection there with. In FIG. 4A, a stimulation waveform 302 is illustrated with a series of excitation pulses 304-306. In the example of FIG. 4A, the excitation pulses 304-306 are illustrated as a single separate stimulation pulses. Optionally, one or more of the excitation pulses 304-306 may include a series of pulses (e.g. a pulse train) provided therein. As explained herein, various parameters defining the excitation pulse may be modified.

FIG. 4A also illustrates a low field potential (LFP) signal 308 that includes evoked responses 310-312 superimposed thereon. The evoked responses 310-312 are generated in response to the excitation pulses 304-306 within the stimulation waveform. The durations of the stimulation pulses 304-306 are shorter than the duration of the corresponding evoked responses 310-312.

The neuronal activity is measured during stimulation, and may represent an impulse response that is generated in response to each stimulus pulse, also called an evoked response. For brain recordings, the evoked response may be superimposed on the underlying, intrinsic LFP signal 308. The LFP signal 308 (and evoked responses 310-312) can be measured from electrodes on a lead connected to a neuromodulation device, and can be processed by recording circuitry (including amplifiers, filters, A/D converters, microprocessors for DSP, and memory), which may be within the implanted pulse generator.

Response Function

In accordance with embodiments herein, the response function calculated at 332 in FIG. 3A may be determined in various manners. By way of example, the response function may be calculated based on cross correlation. Cross-correlation is a measure of similarity of two series as a function of the lag of one relative to the other. Cross-correlation may also be referred to as a sliding dot product or sliding inner-product.

In accordance with embodiments herein, candidate response functions h(t) are identified based on cross-correlation of two waveforms: (1) the input stimulation waveform x(t), and (2) the evoked potential waveform y(t). Assuming a linear, time-invariant system, the response function h(t) is calculated as:

$$h(t)=x(t)*y(t) \qquad \text{[Equation 1]}$$

In Equation 1, the cross correlation (denoted by the symbol (*)) is determined between two complex functions, namely the EP waveform y(t) and the input stimulation waveform x(t). A known relation exists between cross correlation and convolution, permitting Equation 1 to be rewritten as follows:

$$h(t)=x(t)*y(t)=\int_{-\infty}^{\infty}\overline{x}(\tau)y(t+\tau)d\tau \qquad \text{[Equation 2]}$$

In Equation 2, the neuronal response function is defined by the convolution of the complex conjugate (denoted by the symbol $\overline{x}$) of the input stimulation waveform x(t) and the EP waveform y(t+τ), where τ represents an incremental time shift of the EP waveform y(t) relative to the input stimulation waveform x(t). At each incremental shift z of the EP waveform, the input stimulation waveform x(t) and EP waveform y(t) overlap by various amounts. One or more processors of the NS system calculate the overlap area at each incremental shift τ. In the foregoing example, the overlap area may be obtained by calculating an integral of a multiplicative product of the stimulation waveform x(t) and the shifted EP waveform y(t)). Optionally, the overlap area may be calculated in other manners. The value of the neuronal response function h(t) is greatest when there is maximal overlap of the input stimulation waveform x(t) and the shifted EP waveform y(t+τ).

To solve the Equation 2 for the neuronal response function h(t), a deconvolution matrix M may be defined based on the input stimulation waveform x(t) to provide Equation 3:

$$h(t)=M*y(t+\tau) \qquad \text{[Equation 3]}$$

The deconvolution matrix is defined as a function of the input stimulation waveform. Examples of the deconvolution matrix are described below in more detail.

Figure 4C:
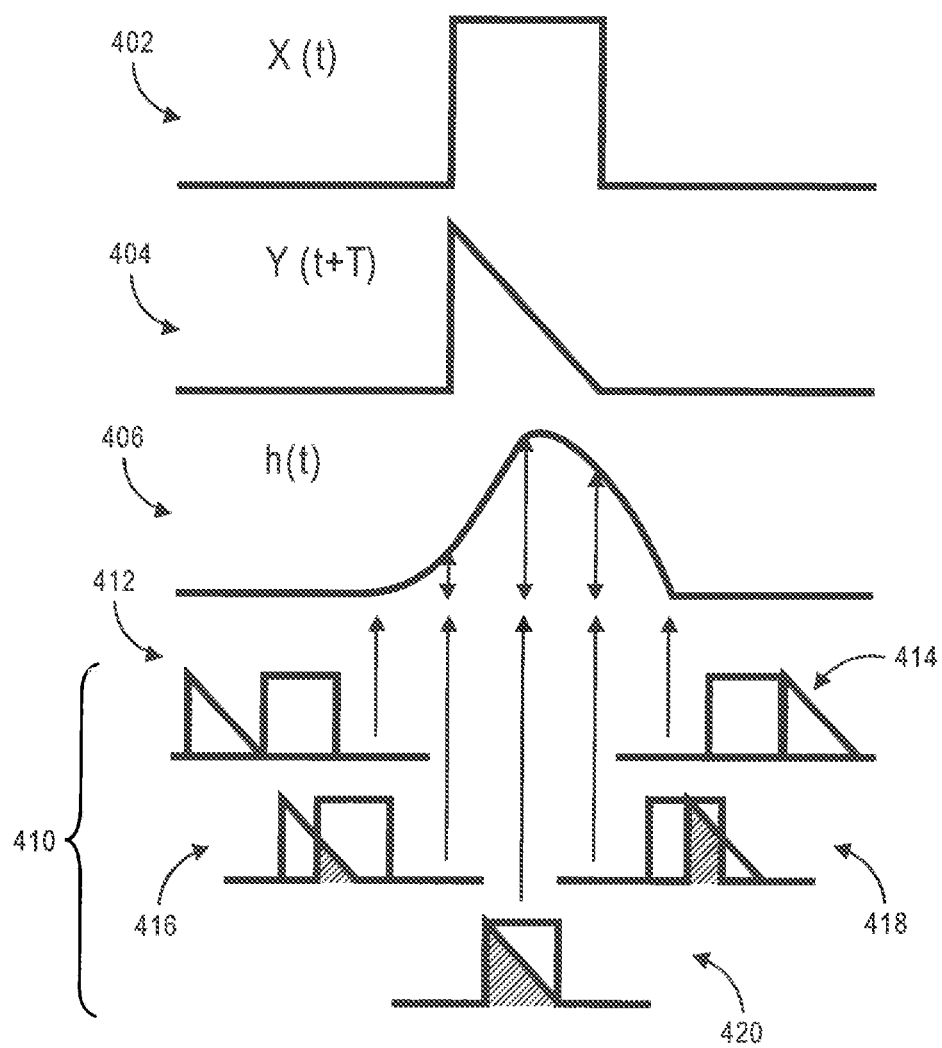
FIG. 4C illustrates a pictorial representation of a comparison between an input stimulation waveform x(t) and an evoked response waveform y(t) to obtain a neuronal response function in accordance with embodiments herein.

FIG. 4C illustrates a pictorial representation of a comparison between an input stimulation waveform x(t) 402 and an evoked response waveform y(t) 404 to obtain a neuronal response function 406. The evoked response waveform y(t+τ) is time shifted by τ relative to the input stimulation waveform x(t). FIG. 4C also illustrates a visual comparison 410 of the cross-correlation between the input stimulation waveform and evoked response waveform at various points in time. At the time denoted by graphics 412 and 414, no overlap occurs. At the time denoted by graphics 416 and 418, partial overlap occurs. At the time denoted by graphics 420, substantially complete overlap occurs.

FIG. 4C illustrates the stimulation waveform 402 to represent a single pulse. Alternatively, the stimulation waveform X(t) 402 may represent a pulse train (e.g., maximal binary length sequences, white noise, or random noise). An example is described herein in connection with utilizing a pulse train defined by a maximum binary length sequence. The duration of the stimulation pulse(s) may be short relative to a time constant of the impulse response characteristic of the neuronal system response.

Optionally, differences may be determined in the response functions relative to a single excitation pulse versus a train of excitation pulses, as the differences may provide insight into a mechanism of action of the stimulation.

Figure 5:
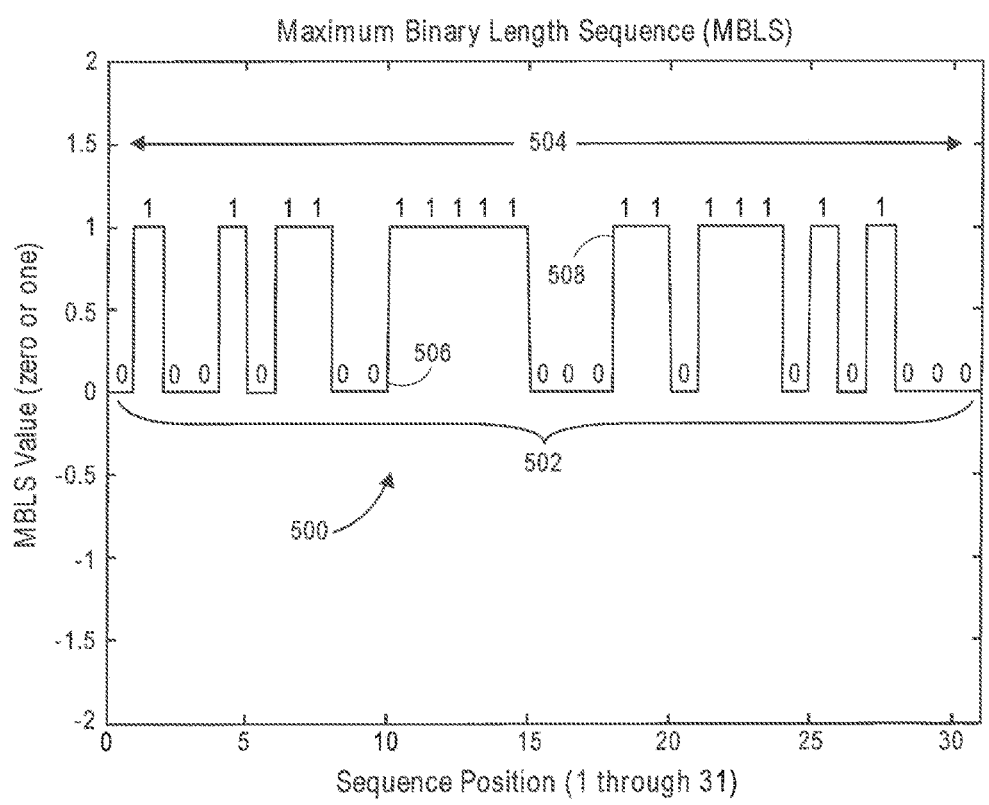
FIG. 5 illustrates an example of a stimulation waveform that may be delivered in accordance with embodiments herein.

FIG. 5 illustrates an example of a stimulation waveform 500 that may be delivered in accordance with embodiments herein. The stimulation waveform 500 represents a pseudorandom binary sequence that comprises a series of excitation pulses 502 delivered as a pulse train and having a corresponding pulse width 504 divided into 31 sequence positions or elements. The excitation pulses 502 include a binary length sequence superimposed thereon. The excitation pulses 502 of the stimulation waveform 500 are modulated between logical zero states 506 and logical one states 508 in accordance with a predetermined pattern. In the example of FIG. 5, the excitation pulses are modulated with the following 31 bit pattern sequence: 0100 1011 0011 1110 0011 0111 0101 000. Optionally, longer or shorter binary length sequences may be used to define the excitation pulses 502 of the stimulation waveform 500. Additionally or alternatively, the modulation pattern sequence may include more than zero and one binary states, namely multiple states (e.g. −1, 0, 1, or −2, −1, 0, 1, 2; etc.).

As discussed in connection with FIG. 3A, while the method varies the neural stimulation parameters when delivering different stimulation waveforms, the stimulation waveform still includes the same bit pattern sequence, even though other neural stimulation parameters may be varied. For example, the amplitude of the excitation pulses may be varied between first and second pulse amplitudes, both of which have the pattern sequence of FIG. 5. Additionally or alternatively, the pulse width may be varied. When the pulse width is varied, the same pattern sequence (e.g., FIG. 5) is used, but with the excitation pulses evenly divided into a number of binary states corresponding to the binary length sequence.

Optionally, different portions of a stimulation waveform may be modulated with different corresponding binary length sequences. For example, when the stimulation waveform represents a burst waveform, the stimulation waveform will include at least two different burst portions. A first burst portion of the stimulation waveform may utilize one binary linked sequence, while the second burst portion of the stimulation waveform utilizes a different binary linked sequence.

In the present example, the length of the binary sequence is 31 bits. Optionally, the length of the binary sequence may be shorter or longer. As one example, a longer binary length sequence may be utilized to provide more detail in connection with complex system responses.

The maximum binary length sequence (MBLS) that is illustrated in FIG. 5 represents one example of a pseudorandom binary sequence that may be utilized to define the pattern of excitation pulses. The pseudorandom binary sequence represents a forcing function that provides a continuous drive to the neuronal region of interest before the system response decays unduly. The pseudorandom random binary sequence may be defined to exhibit therapeutic characteristics. As explained herein, the pseudorandom binary sequence enables simple and fast deconvolution of a system response. The pseudorandom binary sequence allows deconvolution with only a small number of addition operations, without the need for any multiplication or division mathematical operations. For example, a matrix of 31×31 addition operations is utilized for deconvolution of a single EP waveform ensemble average and a corresponding excitation pulse train defined by a 31 bit pseudorandom binary sequence.

In the foregoing examples, the pseudorandom binary sequence is described to represent the excitation pulse sequence that defines the stimulation waveform, where the stimulation waveform switches between a zero amplitude and a maximum amplitude in connection with each logical zero and logical one state. Optionally, the pseudorandom binary sequence may be superimposed on a stimulation waveform where the resultant signal includes a DC bias while switching between the logical one and zero states. For example, the stimulation waveform may represent a burst or tonic therapy, where each stimulation pulse has a positive or negative amplitude. The pseudorandom binary sequence modulates the amplitude of the burst or tonic pulses between first and second positive amplitudes and/or first and second negative amplitudes.

Figure 6:
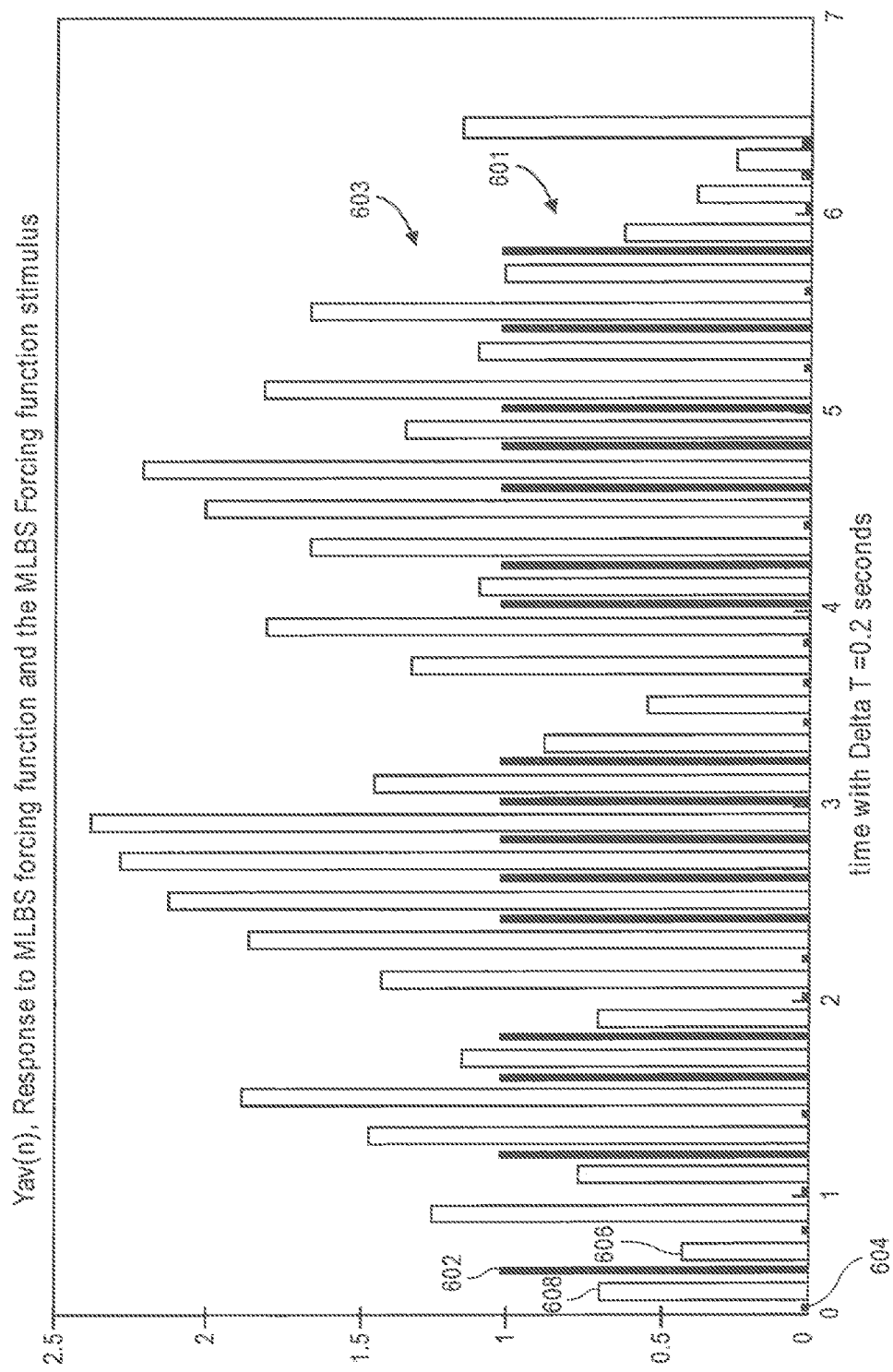
FIG. 6 illustrates an example graph overlaying a maximum length binary sequence (MLBS) forcing function with a corresponding response measured from an evoked potential (EP) waveform in accordance with an embodiment herein.

FIG. 6 illustrates an example graph overlaying a MLBS forcing function 601 with a corresponding response 603 measured from an EP waveform in accordance with an embodiment herein. The MLBS forcing function 601 is illustrated by the dark bars. A portion of the solid/dark bars correspond to a logical one state 602 in the MLBS, while a portion of the solid/dark bars correspond to a logical zero state 604. During a single instance of the logical one state 602, a series of stimuli are delivered. For example, the series of stimuli may include five stimulus delivered at a frequency of 20 Hz. During each instance of a logical one state 602, the corresponding number of stimuli are delivered at the corresponding frequency. During each instance of the logical zero state 604, a series of stimuli are also delivered, but with an amplitude near or at approximately zero. Optionally, the number and frequency of stimuli delivered during each logical one state 602 and each logical zero state 604 may be varied.

The system opens a sensing window (e.g., duration of 50-100 ms, 80 ms, etc.) and measures the EP waveform during the sensing window. The process filters the measured EP waveform to obtain a frequency range of interest. For example, when the sleep spindle activity is of interest, the system utilizes a band pass filter that passes brain wave activity in the 12-15 Hz frequency range. The process then separates the filtered EP waveform into individual element windows that are associated with individual elements in the stimulation waveform. In the example of FIG. 6, individual element windows 606, 608 are shown as open vertical bars. The amplitude of each individual element window 606, 608 correspond to the magnitude of brain wave activity in the pass band of the EP waveform at the corresponding time interval during the sensing window. As a further example, the first individual element window 608 included brain wave activity in the 12-15 Hz range with a magnitude of approximately 0.7, while the magnitude of the next individual element window 606 is approximately 0.4. The process stores a 31 element data value corresponding to the EP waveform measured in the example of FIG. 6.

FIG. 7 illustrates a deconvolution matrix M (Equation 3) that may be utilized to perform deconvolution upon EP waveforms to derive candidate response functions in accordance with embodiments herein. The deconvolution matrix M includes cells arranged in multiple rows and columns, where each cell includes a one or a zero. Each row represents a shifted version of the MLBS forcing function. In the example of FIGS. 5 and 6, the input stimulation waveform utilized a 31 element MLBS force function. Accordingly, the deconvolution matrix 700 represents a 31×31 element matrix with the first row 702 corresponding to the MLBS forcing function used within the stimulation waveform. Each row thereafter corresponds to the preceding row but with a one element circular shift. For example, the second row 704 represents a one element circular shift of the first row 702. Similarly, the third row 706 represents a one element circular shift of the second row 704. The last row 708 represents a 30 element circular shift of the first row 702.

The number of rows and columns in the matrix 700 may be varied based on the number of logical states in the MLBS forcing function. For example, when a 63 element MLBS forcing function is used, the matrix may be a 63×63 element matrix.

The EP waveform (or ensemble average of several EP waveforms) is converted into 31 elements where the amplitude of each element corresponds to an amount of activity in a frequency range of interest. In the example of FIG. 6, the first five elements of the EP waveform would comprise the following approximate values: 0.7, 0.4, 1.25, 0.75 and 1.5.

Figure 8A:
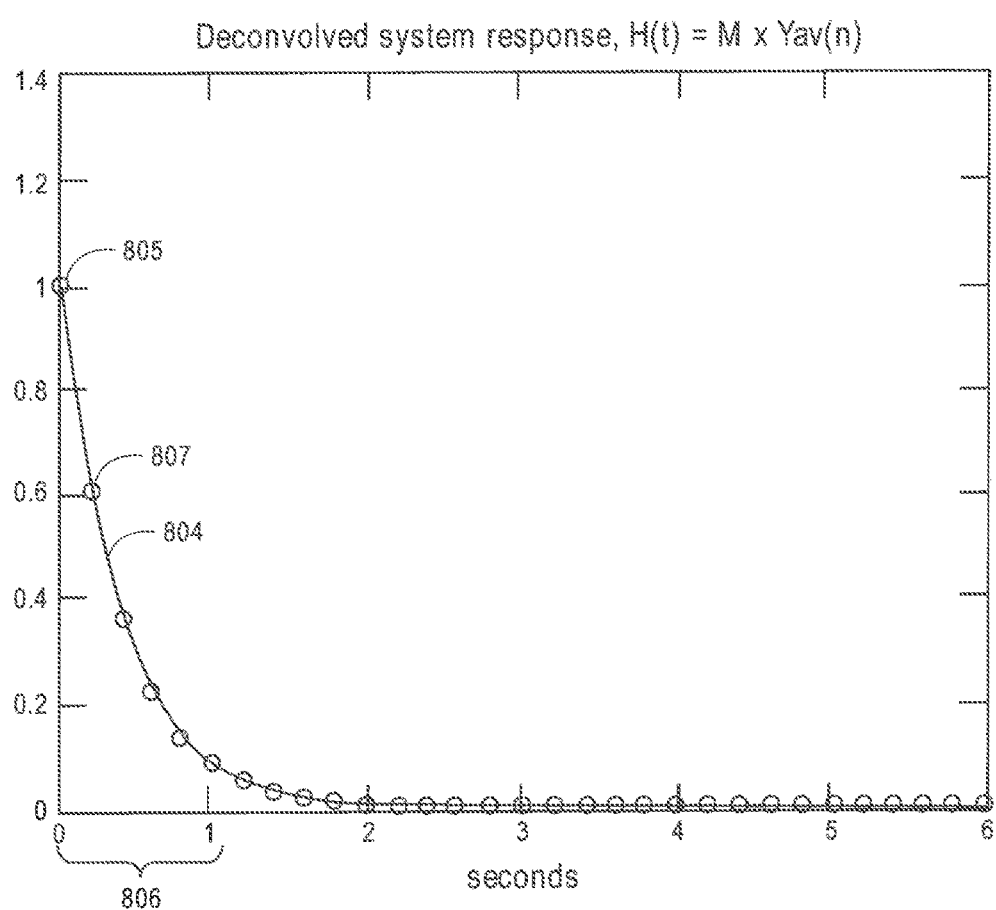
FIG. 8A illustrates an example of candidate response functions that define a neuronal system response determined in accordance with embodiments herein.
Figure 8B:
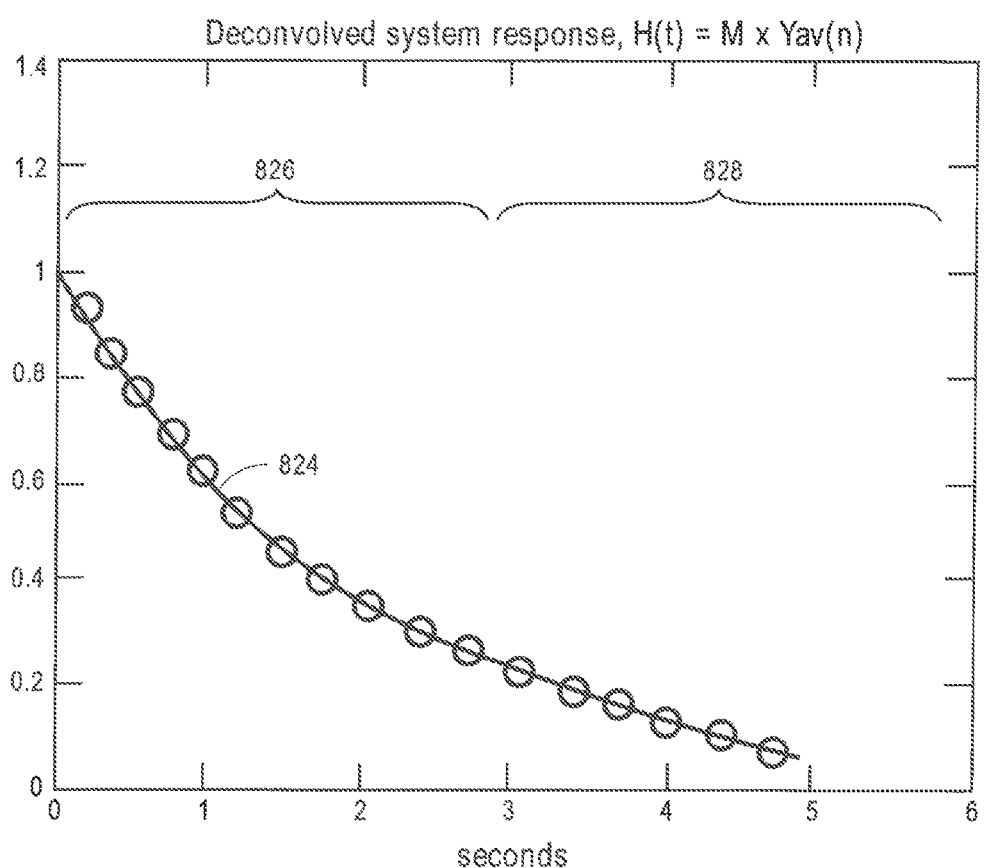
FIG. 8B illustrates an example of candidate response functions that define a neuronal system response determined in accordance with embodiments herein.
Figure 8C:
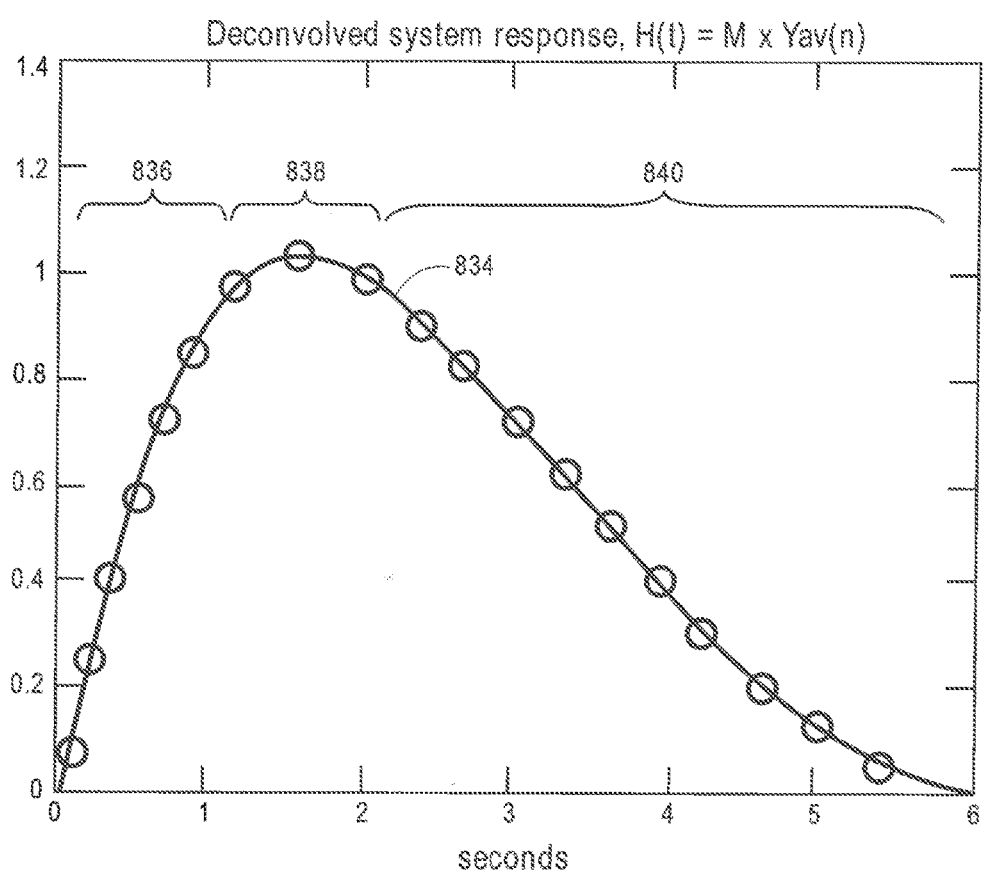
FIG. 8C illustrates an example of candidate response functions that define a neuronal system response determined in accordance with embodiments herein.

FIGS. 8A-8C illustrate examples of candidate response functions that define a neuronal system response determined in accordance with embodiments herein. FIGS. 8A-8C plot time along the horizontal axis and a response magnitude along the vertical axis. Optionally, the response magnitude may be normalized. Within the plots of FIGS. 8A-8C, each data point corresponds to a combination of one row in the deconvolution matrix M and the EP waveform. Each data point in the response functions is formed based on a "sum of products" operation. The 31 elements of the first row of the deconvolution matrix are multiplied by corresponding elements in the EP waveform to form 31 products, which are then summed to form a sum of products value that is recorded as one data point in a response function. Continuing with the example of FIGS. 5 and 6, the first row of the deconvolution matrix is combined with the 31 element EP waveform to form the first data point 805. The second row of the deconvolution matrix is combined with the 31 element EP waveform to form the second data point 807.

As shown in FIG. 8A, a response function 804 begins at a response magnitude of one and decays over approximately a one second period of time 806 to a response magnitude of less than 0.1. A remainder of the response function 804, following the first second of the response period, continues to trail off (e.g. in an exponential manner) to zero. As shown in FIG. 8B, a response function 824 begins at a response magnitude of one and decreases in a somewhat linear manner with a first slope for a first portion 826 of the response interval. Thereafter, the response function 824 decreases in a non-linear manner with a second slope for the remaining interval 828. As illustrated in FIG. 8C, the response function 834 begins with a response magnitude of approximately 0 and increases in a non-linear manner during an initial interval 836. During an intermediate interval 838, the response function 834 maintains a somewhat constant response magnitude over a period of time. At the end of the intermediate interval 838, the response function 834 begins to decrease in a nonlinear manner over a trailing interval 840. In the example of FIG. 8C, the response function 834 begins at approximately 0 and increases over a relatively short period of time to a response magnitude of approximately 1, and thereafter decreases back to a magnitude of approximately zero over a relatively longer period of time.

It is recognized that the neuronal response functions illustrated in FIGS. 8A-8C are merely examples and are not limiting. The response functions 804, 824 and 834 correspond to different neural stimulation parameters utilized during separate iterations through the operations of FIG. 3A. For example, a first EP waveform ensemble may be collected in connection with a first neural stimulation parameter set, to yield the corresponding response function 804 (FIG. 8A). One or more neural stimulation parameters may be adjusted (e.g. electrode configuration, pulse amplitude, pulse width, duty cycle, frequency, etc.), after which a second EP waveform ensemble is collected. The second EP waveform ensemble, when compared with the input stimulation waveform, may yield the response function 824 (FIG. 8B). Further, one or more additional neural stimulation parameters may be adjusted, after which a third EP waveform ensemble is collected. The third EP waveform ensemble may be compared to an input stimulation waveform to yield the response function 834 (FIG. 8C).

Once a sufficient number of neural responses are determined, the process may select a desired one of the system responses that exhibits desirable characteristics. For example, a desirable characteristic of a response function may be to begin at a relatively high response magnitude and reduce quickly to a minimum response magnitude. When the foregoing characteristic is desirable, the process may select the response function of FIG. 8A as desirable. Alternatively, a desirable characteristic of a response function may be to increase from a minimum value to a maximum value relatively quickly and maintain the maximum value for predetermined period of time. When the foregoing characteristic is desirable, the process may select the response function of FIG. 8C. The foregoing represent non-limiting examples of response function characteristics that may be of interest. Additional or alternative characteristics may be utilized to select an individual response function.

Response functions may be chosen to satisfy various objectives. For example, the response function may be utilized, not only to obtain a desired stimulation, but also during implantation to identify the proper location of the stimulation electrodes and/or sensing electrodes. Additionally or alternatively, the response function may be utilized to manage slight changes in electrode location. Additionally or alternatively, the response function may be utilized to detect migration of a lead following implant and/or changes in the physiologic responsiveness of a patient over time.

Figure 9:
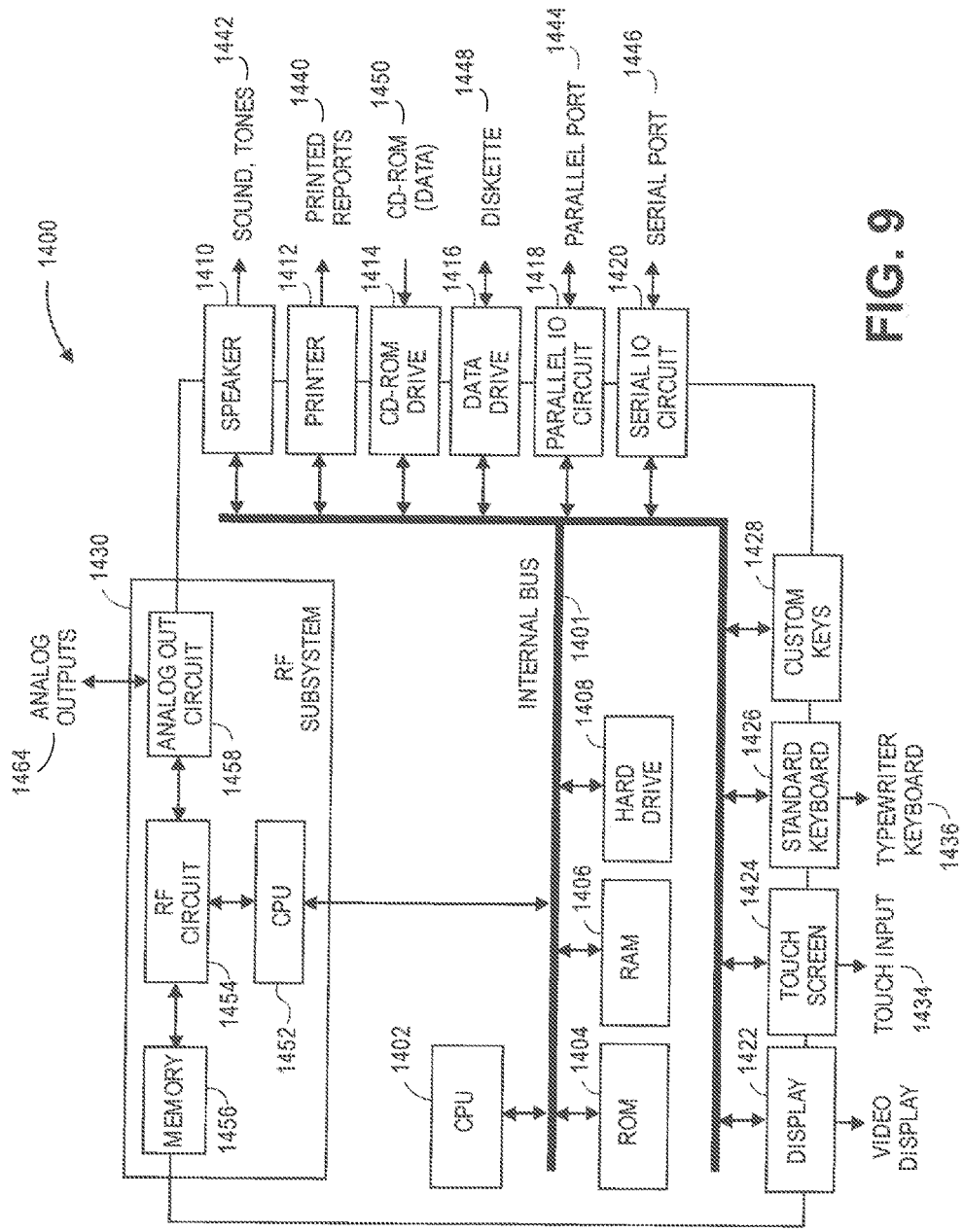
FIG. 9 illustrates a functional block diagram of an external device, according to at least one embodiment, that is operated in accordance with the processes described herein and to interface with the NS system and perform all of a portion of the operations described herein.

FIG. 9 illustrates a functional block diagram of an external device 1400, according to at least one embodiment, that is operated in accordance with the processes described herein and to interface with the NS system and perform all of a portion of the operations described herein. The external device 1400 may be similar to and/or the same as the external device 160. The external device 1400 may be a workstation, a portable computer, a tablet computer, a PDA, a cell phone and the like. The external device 1400 includes an internal bus 1401 that may connect/interface with a Central Processing Unit ("CPU") 1402, ROM 1404, RAM 1406, a hard drive 1408, a speaker 1410, a printer 1412, a CD-ROM drive 1414, a floppy drive 1416, a parallel I/O circuit 1418, a serial I/O circuit 1420, the display 1422, a touchscreen 1424, a standard keyboard 1426, custom keys 1428, and an RF subsystem 1430. The internal bus 1401 is an address/data bus that transfers information between the various components described herein. The hard drive 1408 may store operational programs as well as data, such as stimulation waveform templates and detection thresholds.

The CPU 1402 typically includes a microprocessor, a micro-controller, or equivalent control circuitry, designed specifically to control interfacing with the external device 1400 and with the NS system 100. The CPU 1402 may include RAM or ROM memory, logic and timing circuitry, state machine circuitry, and I/O circuitry to interface with the NS system 100. The CPU 1402 may perform all or a portion of the operations described in connection with FIGS. 3A-8C.

The display 1422 displays various information related to the processes described herein. The touchscreen 1424 may display graphic information relating to the NS system 100 (e.g., stimulation levels, stimulation waveforms, evoked potential measurements) and include a graphical user interface. The graphical user interface may include graphical icons, scroll bars, buttons, and the like which may receive or detect user or touch inputs 1434 for the external device 1400 when selections are made by the user. Optionally the touchscreen 1424 may be integrated with the display 1422. The keyboard 1426 (e.g., a typewriter keyboard 1436) allows the user to enter data to the displayed fields, as well as interface with the RF subsystem 1430. Furthermore, custom keys 1428, for example, may turn on/off the external device 1400. The printer 1412 prints copies of reports 1440 for a physician to review or to be placed in a patient file, and the speaker 1410 provides an audible warning (e.g., sounds and tones 1442) to the user. The parallel I/O circuit 1418 interfaces with a parallel port 1444. The serial I/O circuit 1420 interfaces with a serial port 1446. The floppy drive 1416 accepts diskettes 1448. Optionally, the serial L/O port may be coupled to a USB port or other interface capable of communicating with a USB device such as a memory stick. The CD-ROM drive 1414 accepts CD-ROMs 1450.

The RF subsystem 1430 includes a central processing unit (CPU) 1452 in electrical communication with RF circuitry 1454, which may communicate with both memory 1456 and an analog out circuit 1458. The analog out circuit 1458 includes communication circuits to communicate with analog outputs 1464. The external device 1400 may wirelessly communicate with the NS system 100 using a telemetry system. Additionally or alternatively, the external device 1400 may wirelessly communicate with the NS system 100 utilize wireless protocols, such as Bluetooth, Bluetooth low energy, WiFi, MICS, and the like. Alternatively, a hardwired connection may be used to connect the external device 1400 to the NS system 100.

Optionally, the external device 1400 may transmit the stimulation database request to the IPG 150. For example, the user may instruct the external device 1400 to transmit a stimulation database request from the graphical user interface on the touchscreen 1424, the keyboard 1426, or the like. The NS system 100 receives the request via the communication circuitry 155 (e.g., the RF subsystem 1430, RF circuitry 1454) and transmits the stimulation database stored on the memory 158 to the external device 1400.

The controller 151, the CPU 1402, and the CPU 1452 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controller 151, the CPU 1402, and the CPU 1452 may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controller 151, the CPU 1402, and the CPU 1452 may execute a set of instructions that are stored in one or more storage elements, in order to process data. The storage elements may also store data or other information as desired or needed. The storage element may be in the form of an information source or a physical memory element within the controller 151, the CPU 1402, and the CPU 1452. The set of instructions may include various commands that instruct the controller 151, the CPU 1402, and the CPU 1452 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second." and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method of providing an electrical stimulation therapy for a patient for a neuronal region of interest (ROI), the method comprising:
   positioning an electrode proximate to the neuronal ROI, wherein the electrode is electrically coupled to a neurostimulation (NS) system;
   delivering, from the NS system, a stimulation waveform to the electrode based on NS parameters to stimulate nerve tissue of the patient, wherein (1) the stimulation waveform is generated by producing a series of pulses controlled by a pseudo random binary sequence and (2) each respective pulse of the stimulation waveform is generated to exhibit a zero pulse amplitude or a maximum pulse amplitude according to a corresponding bit in the pseudo random binary sequence;
   measuring an evoked potential waveform resulting from the stimulation waveform;
   identifying a neuronal system response for the neuronal ROI based on the pseudo random binary sequence and the evoked potential;
   determining a carry over window of a therapeutic effect based on the neuronal system response; and
   programming the NS system to deliver an electrical stimulation therapy including a duty cycle defined by the determined carry over window.

2. The method of claim 1, wherein the identifying comprises performing a cross correlation analysis between the pseudo random binary sequence and the corresponding evoked potential waveform to obtain the neuronal system response.

3. The method of claim 1, wherein the identifying includes applying a deconvolution matrix to the evoked potential waveform in order to derive the neuronal system response.

4. The method of claim 1 further comprising:
   performing ensemble averaging between multiple pseudo random binary sequences and corresponding neuronal responses.

5. The method of claim 1 wherein the duty cycle is defined by a calculated amount of time that a therapeutic benefit is maintained after electrical stimulation ceases.

6. The method of claim 5 wherein the therapeutic benefit is related to an amount of neuronal activity within a limited frequency band.

7. A system for electrical stimulation of nerve tissue of a patient, the system comprising:
   a stimulation lead comprising an electrode configured to be positioned proximate to a neuronal region of interest (ROI);
   an implantable pulse generator (IPG) electrically coupled to the stimulation lead, wherein the IPG comprises one or more processors for controlling operations of the IPG, pulse generating circuitry for generating electrical pulses, and sensing circuitry for sensing neuronal activity, and wherein the IPG is configured to:
   (A) deliver a stimulation waveform based on neurostimulation (NS) parameters, wherein (1) the stimulation waveform is generated by producing a series of pulses controlled by a pseudo random binary sequence and (2) each respective pulse of the stimulation waveform is generated to exhibit a zero pulse amplitude or a maximum pulse amplitude according to a corresponding bit in the pseudo random binary sequence; (B) measure an evoked potential waveform resulting from the stimulation waveform; (C) identify a neuronal system response for the neuronal ROI based on the pseudo random binary sequence and the evoked potential; (D) determine a carry over window of a therapeutic effect based on the neuronal system response; and (E) deliver an electrical stimulation therapy including a duty cycle defined by the determined carry over window.

8. The system of claim 7, wherein the IPG performs a cross correlation analysis between the pseudo random binary sequence and the corresponding evoked potential waveform to obtain the neuronal system response.

9. The system of claim 7, wherein the IPG applies a deconvolution matrix to the evoked potential waveform in order to derive the neuronal system response.

10. The system of claim 7 wherein the IPG is configured to perform ensemble averaging between multiple pseudo random binary sequences and corresponding neuronal responses.

11. The system of claim 7 wherein IPG is configured to define the duty cycle using a calculated amount of time that a therapeutic benefit is maintained after electrical stimulation ceases.

12. The system of claim 11 wherein the therapeutic benefit is related to an amount of neuronal activity within a limited frequency band.

* * * * *